United States Patent
Reutzel-Edens

(10) Patent No.: US 9,573,970 B2
(45) Date of Patent: Feb. 21, 2017

(54) 4-{4-[(1E)-4-(2,9-DIAZASPIRO[5.5]UNDEC-2-YL)BUT-1-EN-1-YL]-2-METHYLBENZYL}-5-(PROPAN-2-YL)-1H-PYRAZOL-3-YL BETA-D GLUCOPYRANOSIDE ACETATE

(71) Applicant: Eli Lilly and Company, Indianapolis, IN (US)

(72) Inventor: Susan Marie Reutzel-Edens, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 15/026,427

(22) PCT Filed: Oct. 30, 2014

(86) PCT No.: PCT/US2014/063161
§ 371 (c)(1),
(2) Date: Mar. 31, 2016

(87) PCT Pub. No.: WO2015/069541
PCT Pub. Date: May 14, 2015

(65) Prior Publication Data
US 2016/0215011 A1    Jul. 28, 2016

Related U.S. Application Data

(60) Provisional application No. 61/901,488, filed on Nov. 8, 2013.

(51) Int. Cl.
C07H 17/02    (2006.01)
(52) U.S. Cl.
CPC ............ C07H 17/02 (2013.01); C07B 2200/13 (2013.01)
(58) Field of Classification Search
None
See application file for complete search history.

(56) References Cited

U.S. PATENT DOCUMENTS

| | | | |
|---|---|---|---|
| 7,087,579 B2 | 8/2006 | Nishimura et al. | |
| 7,115,575 B2 | 10/2006 | Fujikura et al. | |
| 7,217,697 B2 | 5/2007 | Shiohara et al. | |
| 7,635,684 B2 | 12/2009 | Fushimi et al. | |
| 7,655,632 B2 | 2/2010 | Teranishi et al. | |
| 7,820,804 B2 | 10/2010 | Brummerhop et al. | |
| 8,697,849 B2 * | 4/2014 | Qu ................ | A61K 31/706 536/17.4 |
| 9,296,775 B2 * | 3/2016 | Qu ................ | A61K 31/706 |
| 2010/0279962 A1 | 11/2010 | Takeuchi et al. | |
| 2014/0162967 A1 | 6/2014 | Qu | |

FOREIGN PATENT DOCUMENTS

| | | |
|---|---|---|
| EP | 1544208 | 7/2003 |
| WO | WO2005121161 | 12/2005 |
| WO | WO2007136116 | 11/2007 |
| WO | WO2010095768 | 8/2010 |
| WO | WO2011039338 | 4/2011 |
| WO | WO2011048112 | 4/2011 |
| WO | WO2013169546 | 11/2013 |

OTHER PUBLICATIONS

Chao, Edward C. and Henry, Robert R., Nature Reviews., vol. 9, Jul. 2010, pp. 551-559.

* cited by examiner

Primary Examiner — Traviss C McIntosh, III
(74) Attorney, Agent, or Firm — Nelsen L Lentz

(57) ABSTRACT

The present invention provides a compound of Formula I or hydrate thereof, useful for the treatment of diabetes.

Formula I

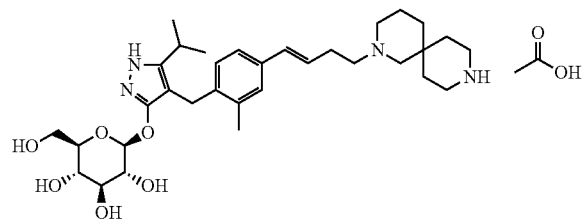

7 Claims, No Drawings

4-{4-[(1E)-4-(2,9-DIAZASPIRO[5.5]UNDEC-2-YL)BUT-1-EN-1-YL]-2-METHYLBENZYL}-5-(PROPAN-2-YL)-1H-PYRAZOL-3-YL BETA-D GLUCOPYRANOSIDE ACETATE

The present invention relates to a novel SGLT1 inhibitor which is an acetate salt of a pyrazole compound, to pharmaceutical compositions comprising the compound, to methods of using the compound to treat physiological disorders, and to intermediates and processes useful in the synthesis of the compound.

The present invention is in the field of treatment of diabetes and other diseases and disorders associated with hyperglycemia. Diabetes is a group of diseases that is characterized by high levels of blood glucose. It affects approximately 25 million people in the United States and is also the 7th leading cause of death in U.S. according to the 2011 National Diabetes Fact Sheet (U.S. Department of Health and Human Services, Centers for Disease Control and Prevention). Sodium-coupled glucose cotransporters (SGLT's) are one of the transporters known to be responsible for the absorption of carbohydrates, such as glucose. More specifically, SGLT1 is responsible for transport of glucose across the brush border membrane of the small intestine Inhibition of SGLT1 may result in reduced absorption of glucose in the small intestine, thus providing a useful approach to treating diabetes.

U.S. Pat. No. 7,655,632 discloses certain pyrazole derivatives with human SGLT1 inhibitory activity which are further disclosed as useful for the prevention or treatment of a disease associated with hyperglycemia, such as diabetes. In addition, WO 2011/039338 discloses certain pyrazole derivatives with SGLT1/SGLT2 inhibitor activity which are further disclosed as being useful for treatment of bone diseases, such as osteoporosis.

There is a need for alternative drugs and treatment for diabetes. The present invention provides an acetate salt of a pyrazole compound, which is an SGLT1 inhibitor, and as such, may be suitable for the treatment of certain disorders, such as diabetes.

Accordingly, the present invention provides a compound of Formula I:

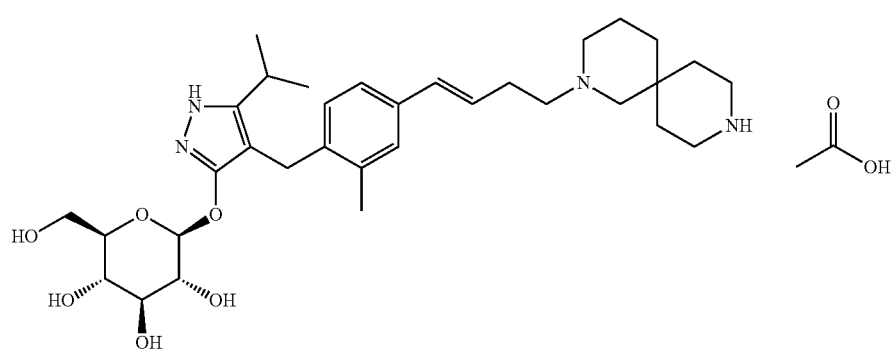

Formula I or hydrate thereof.

The present invention also provides a crystalline form of the compound of Formula I which is hydrated.

In addition, the present invention provides a crystalline form of a compound of Formula I, which is hydrated, characterized by at least one of the following:

a. an X-ray powder diffraction pattern using CuKα radiation having an intense peak at diffraction angle 2-theta of 5.2° in combination with one or more intense peaks selected from the group consisting of 7.8°, 8.0°, and 10.7° (±0.2° respectively); and b. a $^{13}$C solid state NMR spectrum which comprises intense peaks referenced to the highfield resonance of adamantane (δ=29.5 ppm) at: 181.8, 161.2, 160.0, 147.6 and 137.4 ppm (±0.2 ppm respectively).

The present invention further provides a crystalline form of Formula I which is hydrated, wherein the water content at ambient temperature is in the range of about 9% to about 12% by weight.

In addition, the present invention provides a method of treating diabetes in a patient comprising administering to a patient in need of such treatment an effective amount of a compound of Formula I or hydrate thereof. The present invention further provides a method of treating type 1 diabetes in a patient comprising administering to a patient in need of such treatment an effective amount of a compound of Formula I or hydrate thereof. In addition, the present invention provides a method of treating type 2 diabetes in a patient comprising administering to a patient in need of such treatment an effective amount of a compound of Formula I or hydrate thereof. The present invention also provides a method of treating impaired glucose tolerance (IGT), impaired fasting glucose (IFG), or metabolic syndrome in a patient comprising administering to a patient in need of such treatment an effective amount of a compound of Formula I or hydrate thereof.

Furthermore, this invention provides a compound of Formula I or hydrate thereof for use in therapy, in particular for the treatment of diabetes. In addition, this invention provides a compound of Formula I or hydrate thereof for use in the treatment of type 1 diabetes. In addition, this invention provides a compound of Formula I or hydrate thereof for use in the treatment of type 2 diabetes. The invention further provides a compound of Formula I or hydrate thereof for use in the treatment of IGT, IFG, or metabolic syndrome. This invention also provides the use of a compound of Formula I or hydrate thereof for the manufacture of a medicament for the treatment of diabetes. Furthermore, this invention provides the use of a compound of Formula I or hydrate thereof for the manufacture of a medicament for the treatment of type 1 diabetes. This invention also provides the use of a compound of Formula I or hydrate thereof for the manufacture of a medicament for the treatment of type 2 diabetes. The invention also provides the use of a compound of Formula I or hydrate thereof for the manufacture of a medicament for the treatment of IGT, IFG, or metabolic syndrome.

The invention further provides a pharmaceutical composition comprising a compound of Formula I or hydrate thereof with one or more pharmaceutically acceptable carriers, diluents, or excipients. In a particular embodiment, the composition further comprises one or more other therapeutic agents. This invention also encompasses novel intermediates and processes for the synthesis of the compound of Formula I or hydrate thereof.

In addition, the invention provides a process for preparing a crystalline SGLT1 inhibitor, comprising mixing 4-{4-[(1E)-4-(2,9-diazaspiro[5.5]undec-2-yl)but-1-en-1-yl]-2-methylbenzyl}-5-(propan-2-yl)-1H-pyrazol-3-yl beta-D-glucopyranoside with wet ethyl acetate. The invention further provides a process for preparing a crystalline SGLT inhibitor, comprising mixing 4-{4-[(1E)-4-(2,9-diazaspiro[5.5]undec-2-yl)but-1-en-1-yl]-2-methylbenzyl}-5-(propan-2-yl)-1H-pyrazol-3-ylbeta-D-glucopyranoside with wet ethyl acetate, and then collecting the resulting solid.

Isolation and purification of 4-{4-[(1E)-4-(2,9-diazaspiro[5.5]undec-2-yl)but-1-en-1-yl]-2-methylbenzyl}-5-(propan-2-yl)-1H-pyrazol-3-yl beta-D-glucopyranoside (free base) which is an amorphous solid, requires the use of chromatography, which can be resource intensive. The compound of Formula I allows for improvement in isolation and purification through elimination of chromatography, and provides a crystalline form with improved form stability and handling properties for pharmaceutical formulation, in particular commercial manufacture and storage of pharmaceutical compositions.

As used herein, the term "intense peak" means a peak having an intensity that is at least 5% that of the most intense peak in the relevant spectrum or powder pattern.

As used herein, the terms "treating" or "to treat" includes restraining, slowing, stopping, or reversing the progression or severity of an existing symptom or disorder.

As used herein, the term "patient" refers to a mammal, such as a mouse, guinea pig, rat, dog, or human. It is understood that the preferred patient is a human.

As used herein, the term "effective amount" refers to the amount or dose of compound of the invention which, upon single or multiple dose administration to the patient, provides the desired effect in the patient under diagnosis or treatment.

An effective amount can be readily determined by the attending diagnostician, as one skilled in the art, by the use of known techniques and by observing results obtained under analogous circumstances. In determining the effective amount for a patient, a number of factors are considered by the attending diagnostician, including, but not limited to: the species of mammal; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compound of Formula I is generally effective over a wide dosage range. For example, dosages per day normally fall within the range of about 0.01 to about 30 mg/kg of body weight. In some instances dosage levels below the lower limit of the aforesaid range may be more than adequate, while in other cases still larger doses may be employed without causing any harmful side effect, and therefore the above dosage range is not intended to limit the scope of the invention in any way.

The compound of the invention is preferably formulated as a pharmaceutical composition administered by any route which makes the compound bioavailable. Most preferably, such compositions are for oral administration. Such pharmaceutical compositions and processes for preparing same are well known in the art. (See, e.g., Remington: The Science and Practice of Pharmacy (D. B. Troy, Editor, 21st Edition., Lippincott, Williams & Wilkins, 2006).

In a further aspect of the invention, the compound of the present invention may be administered in combination with one or more therapeutic agents, such as antidiabetic agents. Administration in combination includes simultaneous or sequential administration. In addition, simultaneous administration of the combination can be as a single combination dose or separate doses of each therapeutic agent. Examples of antidiabetic agents include metformin; a DPPIV inhibitor, such as sitagliptin or linagliptin; a sulfonylurea, such as glimepiride; a thiazolidinedione, such as pioglitazone; a basal insulin, such as glargine; a rapid acting insulin, such as HUMALOG or NOVOLOG; a GLP-1 agonist, such as exenatide or liraglutide; an SGLT2 inhibitor, such as dapagliflozin or empagliflozin; a glucagon receptor antagonist, such as LY2409021; and the like.

The compound of Formula I can be prepared as illustrated in the preparations, examples, and schemes set forth below. The reagents and starting materials are readily available to one of ordinary skill in the art. All substituents, unless otherwise specified are as previously defined. It is understood that these schemes, preparations, and examples are not intended to be limiting to the scope of the invention in any way.

Examples of resolutions include selective crystallization techniques or chiral chromatography. (See, e.g. J. Jacques, et al., "Enantiomers, Racemates, and Resolutions", John Wiley and Sons, Inc., 1981, and E. L. Eliel and S. H. Wilen, "Stereochemistry of Organic Compounds", Wiley-Interscience, 1994). It should be further clear to one of ordinary skill in the art that separation and isolation, by chromatography, chiral chromatography or selective crystallization, of individual diastereomers or geometric isomers can occur at any convenient point in the synthesis.

As used herein, "δ" refers to parts per million down-field from tetramethylsilane; "min" refers to minute or minutes; "THF" refers to tetrahydrofuran; "MeOH" refers to methanol or methyl alcohol; "HPLC" refers to high-performance liquid chromatography;

The term "Ac" refers to an acetyl substituent of the following structure:

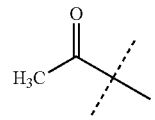

The term "Bz" refers to a benzoyl substituent of the following structure:

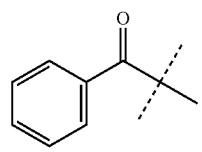

The term "BOC" refers to a t-butyloxycarbonyl protecting group.

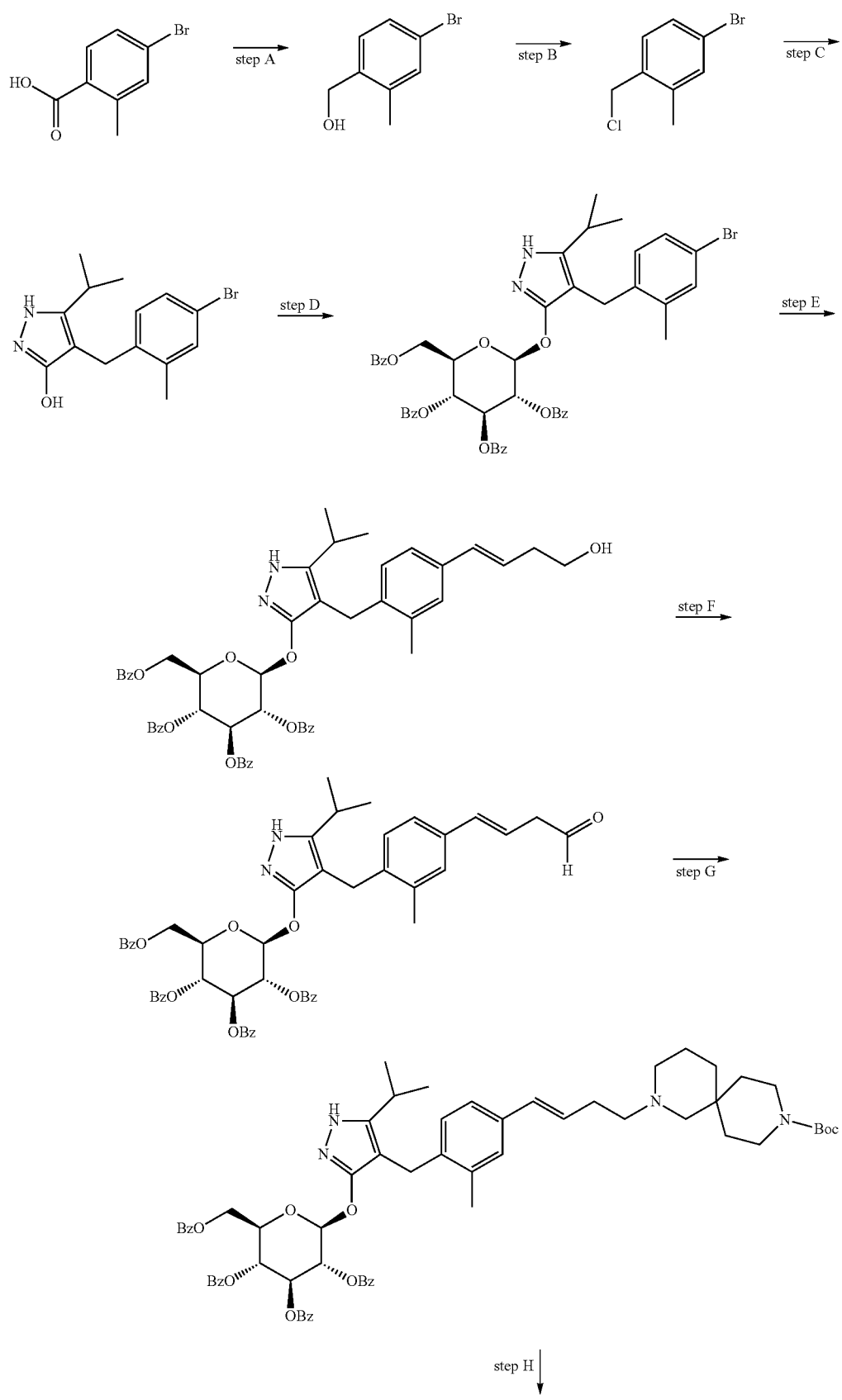

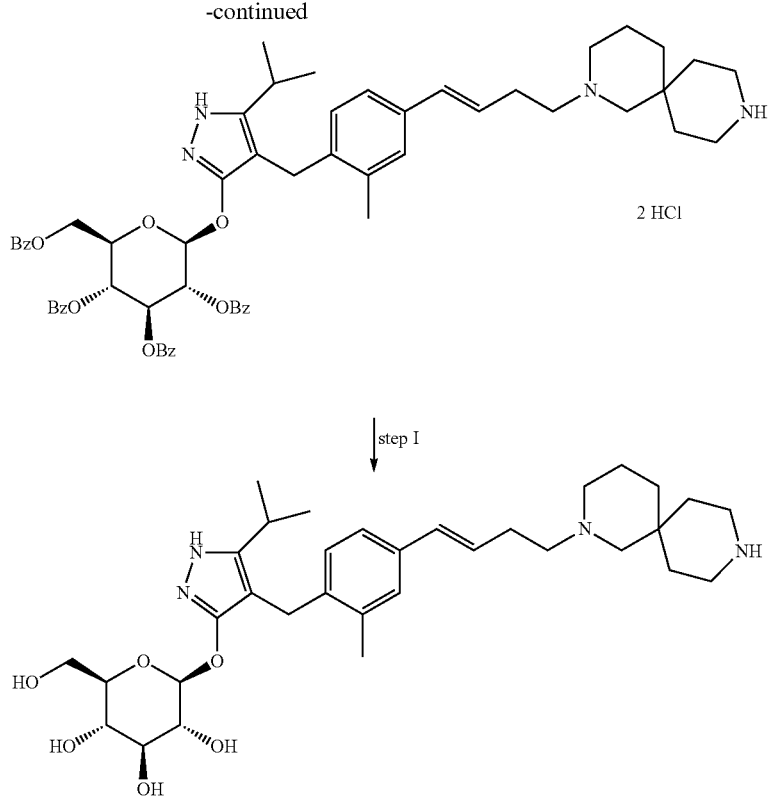

2 HCl step I

Preparation 1

(4-bromo-2-methyl-phenyl)methanol

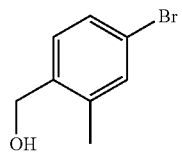

Scheme 1, step A: Add borane-tetrahydrofuran complex (0.2 mol, 200 mL, 1.0 M solution) to a solution of 4-bromo-2-methylbenzoic acid (39 g, 0.18 mol) in tetrahydrofuran (200 mL). After 18 hours at room temperature, remove the solvent under the reduced pressure to give a solid. Purify by flash chromatography to yield the title compound as a white solid (32.9 g, 0.16 mol). $^1$H NMR (CDCl$_3$): δ 1.55 (s, 1H), 2.28 (s, 3H), 4.61 (s, 2H), 7.18-7.29 (m, 3H).

Alternative Synthesis of (4-bromo-2-methyl-phenyl)methanol

Borane-dimethyl sulfide complex (2M in THF; 116 mL, 0.232 mol) is added slowly to a solution of 4-bromo-2-methylbenzoic acid (24.3 g, 0.113 mol) in anhydrous tetrahydrofuran (THF, 146 mL) at 3° C. After stirring cold for 10 min the cooling bath is removed and the reaction is allowed to warm slowly to ambient temperature. After 1 hour, the solution is cooled to 5° C., and water (100 mL) is added slowly. Ethyl acetate (100 mL) is added and the phases are separated. The organic layer is washed with saturated aqueous NaHCO$_3$ solution (200 mL) and dried over Na$_2$SO$_4$. Filtration and concentration under reduced pressure gives a residue which is purified by filtration through a short pad of silica eluting with 15% ethyl acetate/iso-hexane to give the title compound (20.7 g, 91.2% yield). MS (m/z): 183/185 (M+1-18).

Preparation 2

4-bromo-1-chloromethyl-2-methyl-benzene

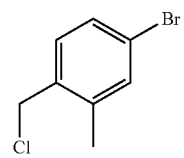

Scheme 1, step B: Add thionyl chloride (14.31 mL, 0.2 mol), to a solution of (4-bromo-2-methyl-phenyl)methanol (32.9 g, 0.16 mol) in dichloromethane (200 mL) and dimethylformamide (0.025 mol, 2.0 mL) at 0° C. After 1 hour at room temperature pour the mixture into ice-water (100 g), extract with dichloromethane (300 mL), wash extract with 5% aq. sodium bicarbonate (30 mL) and brine (200 mL), dry over sodium sulfate, and concentrate under reduced pressure to give the crude title compound as a white solid (35.0 g, 0.16 mol). The material is used for the next step of reaction without further purification. $^1$H NMR (CDCl$_3$): δ 2.38 (s, 3H), 4.52 (s, 2H), 7.13-7.35 (m, 3H).

Alternative Synthesis of 4-bromo-1-chloromethyl-2-methyl-benzene

Methanesulfonyl chloride (6.83 mL, 88.3 mmol) is added slowly to a solution of (4-bromo-2-methyl-phenyl)methanol (16.14 g, 80.27 mmol) and triethylamine (16.78 mL; 120.4 mmol) in dichloromethane (80.7 mL) cooled in ice/water. The mixture is allowed to slowly warm to ambient temperature and is stirred for 16 hours. Further methanesulfonyl chloride (1.24 mL; 16.1 mmol) is added and the mixture is stirred at ambient temperature for 2 hours. Water (80 mL) is added and the phases are separated. The organic layer is washed with hydrochloric acid (1N; 80 mL) then saturated aqueous sodium hydrogen carbonate solution (80 mL), then water (80 mL), and is dried over Na$_2$SO$_4$. Filtration and concentration under reduced pressure gives a residue which is purified by flash chromatography (eluting with hexane) to give the title compound (14.2 g; 80.5% yield). $^1$H NMR (300.11 MHz, CDCl$_3$): δ 7.36-7.30 (m, 2H), 7.18 (d, J=8.1 Hz, 1H), 4.55 (s, 2H), 2.41 (s, 3H).

Preparation 3

4-[(4-bromo-2-methyl-phenyl)methyl]-5-isopropyl-1H-pyrazol-3-ol

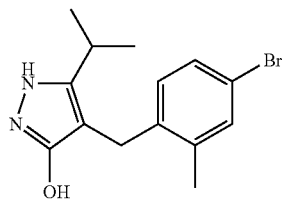 [SMILES: Cc1cc(Br)ccc1Cc1c(O)n[nH]c1C(C)C]

Scheme 1, step C: Add sodium hydride (8.29 g, 0.21 mol, 60% dispersion in oil) to a solution of methyl 4-methyl-3-oxovalerate (27.1 mL, 0.19 mol) in tetrahydrofuran at 0° C. After 30 min at room temperature, add a solution of 4-bromo-1-chloromethyl-2-methyl-benzene (35.0 g, 0.16 mol) in tetrahydrofuran (50 mL). Heat the resulting mixture at 70° C. overnight (18 hours). Add 1.0 M HCl (20 mL) to quench the reaction. Extract with ethyl acetate (200 mL), wash extract with water (200 mL) and brine (200 mL), dry over Na$_2$SO$_4$, filter and concentrate under reduced pressure. Dissolve the resulting residue in toluene (200 mL) and add hydrazine monohydrate (23.3 mL, 0.48 mol). Heat the mixture at 120° C. for 2 hours with a Dean-Stark apparatus to remove water. Cool and remove the solvent under the reduced pressure, dissolve the residue with dichloromethane (50 mL) and methanol (50 mL). Pour this solution slowly to a beaker with water (250 mL). Collect the resulting precipitated product by vacuum filtration. Dry in vacuo in an oven overnight at 40° C. to yield the title compound as a solid (48.0 g, 0.16 mol). MS (m/z): 311.0 (M+1), 309.0 (M−1).

Alternative Synthesis of 4-[(4-bromo-2-methyl-phenyl)methyl]-5-isopropyl-1H-pyrazol-3-ol A solution of 4-bromo-1-chloromethyl-2-methyl-benzene (13.16 g, 59.95 mmoles) in acetonitrile (65.8 mL) is prepared. Potassium carbonate (24.86 g, 179.9 mmol), potassium iodide (11.94 g, 71.94 mmol) and methyl 4-methyl-3-oxovalerate (8.96 mL; 62.95 mmol) are added. The resulting mixture is stirred at ambient temperature for 20 hours. Hydrochloric acid (2N) is added to give pH 3. The solution is extracted with ethyl acetate (100 ml), the organic phase is washed with brine (100 ml) and dried over Na$_2$SO$_4$. The mixture is filtered and concentrated under reduced pressure. The residue is dissolved in toluene (65.8 mL) and hydrazine monohydrate (13.7 mL, 0.180 mol) is added. The resulting mixture is heated to reflux and water is removed using a Dean and Stark apparatus. After 3 hours the mixture is cooled to 90° C. and additional hydrazine monohydrate (13.7 mL; 0.180 mol) is added and the mixture is heated to reflux for 1 hour. The mixture is cooled and concentrated under reduced pressure. The resulting solid is triturated with water (200 mL), filtered and dried in a vacuum oven over P$_2$O$_5$ at 60° C. The solid is triturated in iso-hexane (200 mL) and filtered to give the title compound (14.3 g; 77.1% yield). MS (m/z): 309/311 (M+1).

Preparation 4

4-(4-bromo-2-methylbenzyl)-5-(propan-2-yl)-1H-pyrazol-3-yl 2,3,4,6-tetra-O-benzoyl-beta-D-glucopyranoside

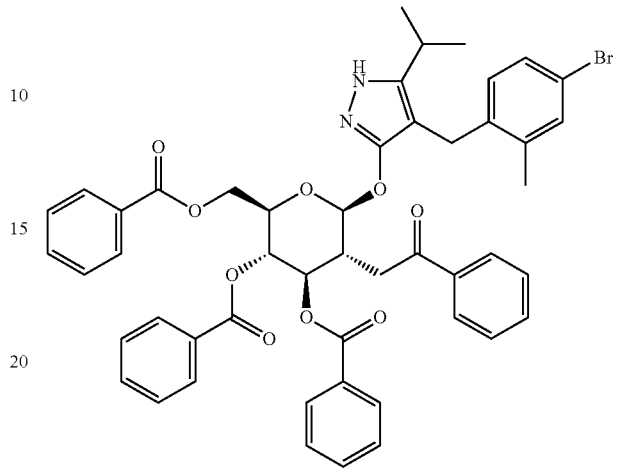

Scheme 1, step D: To a 1 L flask, add 4-[(4-bromo-2-methyl-phenyl)methyl]-5-isopropyl-1H-pyrazol-3-ol (20 g, 64.7 mmol), alpha-D-glucopyranosyl bromide tetrabenzoate (50 g, 76 mmol), benzyltributylammonium chloride (6 g, 19.4 mmol), dichloromethane (500 mL), potassium carbonate (44.7 g, 323 mmol) and water (100 mL). Stir the reaction mixture overnight at room temperature. Extract with dichloromethane (500 mL). Wash extract with water (300 mL) and brine (500 mL). Dry organic phase over sodium sulfate, filter, and concentrate under reduced pressure. Purify the residue by flash chromatography to yield the title compound (37 g, 64 mmol). MS (m/z): 889.2 (M+1), 887.2 (M−1).

Preparation 5

4-{4-[(1E)-4-hydroxybut-1-en-1-yl]-2-methylbenzyl}-5-(propan-2-yl)-1H-pyrazol-3-yl 2,3,4,6-tetra-O-benzoyl-beta-D-glucopyranoside

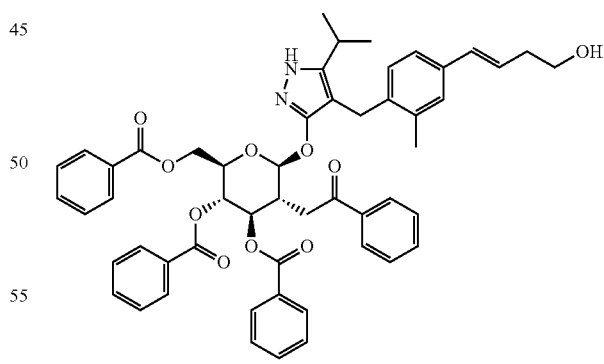

Scheme 1, step E: Add 3-buten-1-ol (0.58 mL, 6.8 mmol) to a solution of 4-(4-bromo-2-methylbenzyl)-5-(propan-2-yl)-1H-pyrazol-3-yl 2,3,4,6-tetra-O-benzoyl-beta-D-glucopyranoside (3 g, 3.4 mmol) in acetonitrile (30 mL) and triethylamine (20 mL). Degas the solution with nitrogen over 10 minutes. Add tri-o-tolylphosphine (205 mg, 0.67 mmol) and palladium acetate (76 mg, 0.34 mmol). Reflux at 90° C. for 2 hours. Cool to room temperature and concentrate to remove the solvent under the reduced pressure.

Purify the residue by flash chromatography to yield the title compound (2.1 g, 2.4 mmol). MS (m/z): 878.4 (M+1).

Preparation 6

4-{4-[(1E)-4-oxybut-1-en-1-yl]-2-methylbenzyl}-5-(propan-2-yl)-1H-pyrazol-3-yl 2,3,4,6-tetra-O-benzoyl-beta-D-glucopyranoside

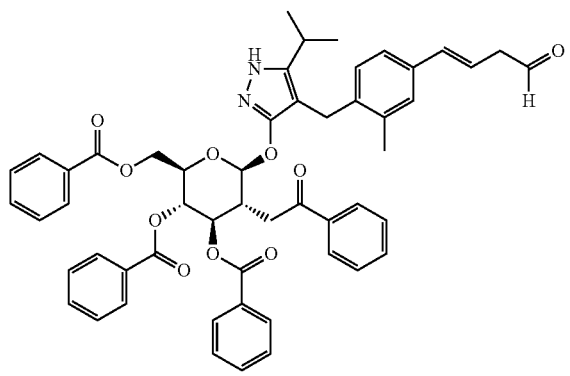 [SMILES: Cc1cc(/C=C/CC=O)ccc1Cc1c(O[C@@H]2O[C@H](COC(=O)c3ccccc3)[C@@H](OC(=O)c3ccccc3)[C@H](OC(=O)c3ccccc3)[C@H]2CC(=O)c2ccccc2)n[nH]c1C(C)C]

Scheme 1, step F: Add 3,3,3-triacetoxy-3-iodophthalide (134 mg, 0.96 mmol) to a solution of 4-{4-[(1E)-4-hydroxybut-1-en-1-yl]-2-methylbenzyl}-5-(propan-2-yl)-1H-pyrazol-3-yl 2,3,4,6-tetra-O-benzoyl-beta-D-glucopyranoside (280 mg, 0.32 mmol) and sodium bicarbonate (133.8 mg, 1.6 mmol) in dichloromethane (20 mL) at 0° C. After 15 minutes at room temperature, quench the reaction with saturated aqueous sodium thiosulfate (10 mL). Extract with dichloromethane (30 mL). Wash extract with water (30 mL) and brine (40 mL). Dry organic phase over sodium sulfate, filter, and concentrate under reduced pressure. Purify the resulting residue by flash chromatography to yield the title compound (270 mg, 0.31 mmol). MS (m/z): 876.5 (M+1), 874.5 (M−1).

Preparation 7 tert-butyl 2-{(3E)-4-[3-methyl-4-({5-(propan-2-yl)-3-[(2,3,4,6-tetra-O-benzoyl-beta-D-glucopyranosyl)oxy]-1H-pyrazol-4-yl}methyl)phenyl]but-3-en-1-yl}-2,9-diazaspiro[5.5]undecane-9-carboxylate

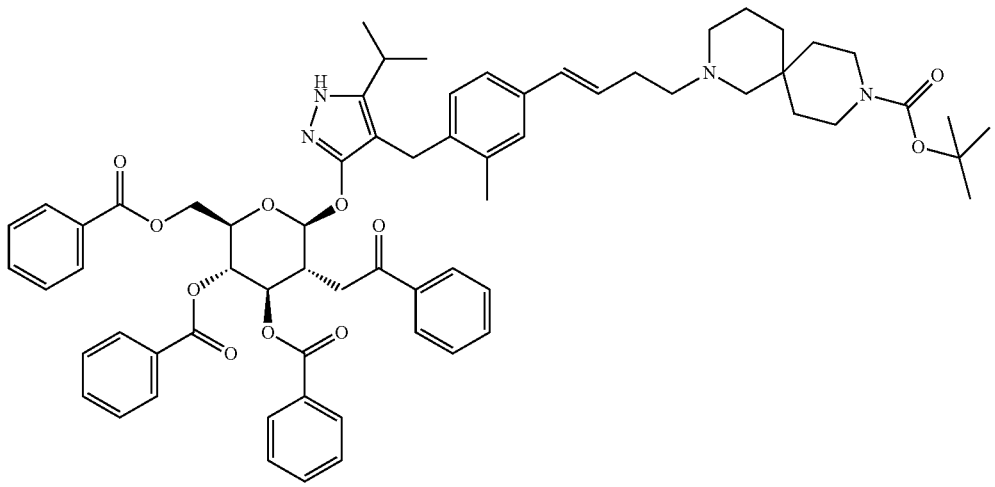 [SMILES: Cc1cc(/C=C/CCN2CCCC3(CCN(C(=O)OC(C)(C)C)CC3)C2)ccc1Cc1c(O[C@@H]2O[C@H](COC(=O)c3ccccc3)[C@@H](OC(=O)c3ccccc3)[C@H](OC(=O)c3ccccc3)[C@H]2CC(=O)c2ccccc2)n[nH]c1C(C)C]

Scheme 1, step G: Add sodium triacetoxyborohydride (98 mg, 0.46 mmol) to a solution of 4-{4-[(1E)-4-oxybut-1-en-1-yl]-2-methylbenzyl}-5-(propan-2-yl)-1H-pyrazol-3-yl 2,3,4,6-tetra-O-benzoyl-beta-D-glucopyranoside (270 mg, 0.31 mmol) and tert-butyl 2,9-diazaspiro[5.5]undecane-9-carboxylate hydrochloride (179 mg, 0.62 mmol) in 1,2-dichloroethane (5 mL). After 30 minutes at room temperature, quench the reaction with saturated aqueous sodium bicarbonate (10 mL). Extract with dichloromethane (30 mL). Wash extract with water (30 mL) and brine (40 mL), dry organic phase over sodium sulfate, filter and concentrate under reduced pressure. Purify the resulting residue by flash chromatography to yield the title compound (275 mg, 0.25 mmol).

MS (m/z): 1115.6 (M+1).

Preparation 8

4-{4-[(1E)-4-(2,9-diazaspiro[5.5]undec-2-yl)but-1-en-1-yl]-2-methylbenzyl}-5-(propan-2-yl)-1H-pyrazol-3-yl 2,3,4,6-tetra-O-benzoyl-beta-D-glucopyranoside dihydrochloride

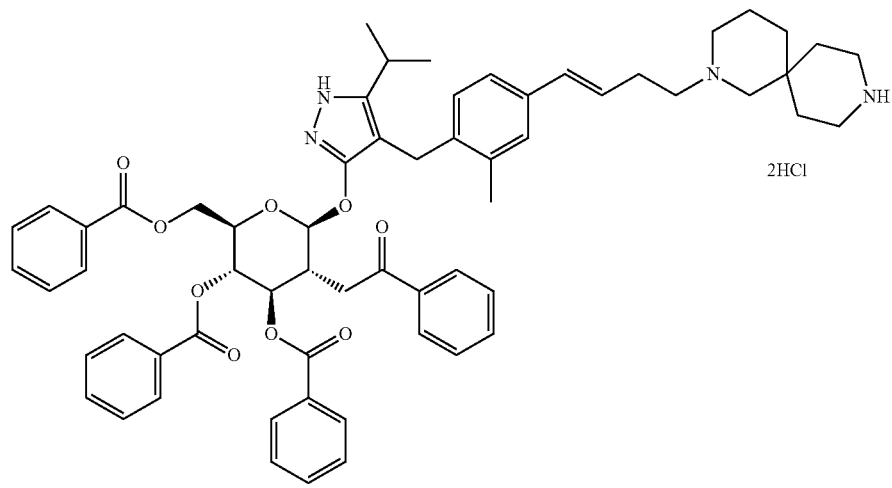 [SMILES: Cc1cc(/C=C/CCN2CCCC3(CCNCC3)C2)ccc1Cc1c(O[C@@H]2O[C@H](COC(=O)c3ccccc3)[C@@H](OC(=O)c3ccccc3)[C@H](OC(=O)c3ccccc3)[C@H]2CC(=O)c2ccccc2)n[nH]c1C(C)C]

Scheme 1, step H: Add hydrogen chloride (4.0 M solution in 1,4-dioxane, 0.6 mL, 2.4 mmol) to a solution of tert-butyl 2-{(3E)-4-[3-methyl-4-({5-(propan-2-yl)-3-[(2,3,4,6-tetra-O-benzoyl-beta-D-glucopyranosyl)oxy]-1H-pyrazol-4-yl}methyl)phenyl]but-3-en-1-yl}-2,9-diazaspiro[5.5]undecane-9-carboxylate (275 mg, 0.25 mmol) in dichloromethane (5 mL). After overnight (18 hours) at room temperature, concentrate to remove the solvent under reduced pressure to yield the title compound as a solid (258 mg, 0.24 mmol). MS (m/z): 1015.6 (M+1).

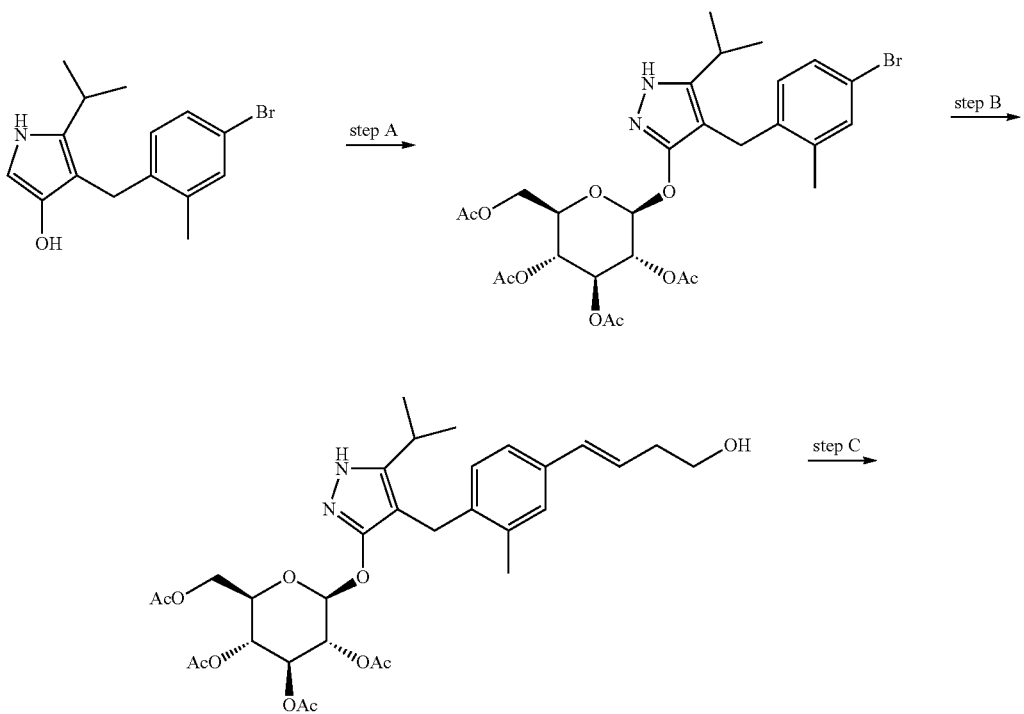

-continued
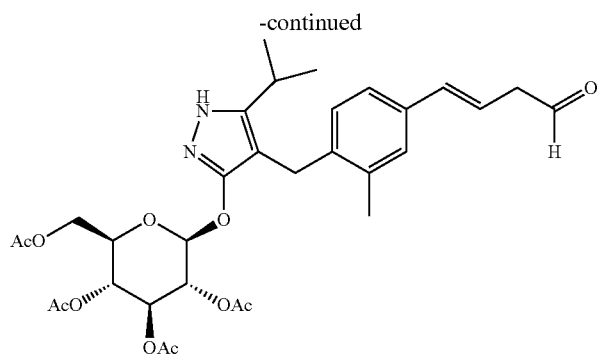
↓ step D
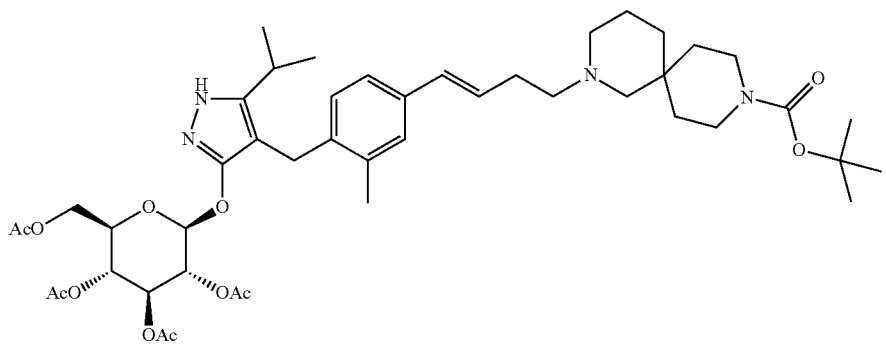
↓ step E
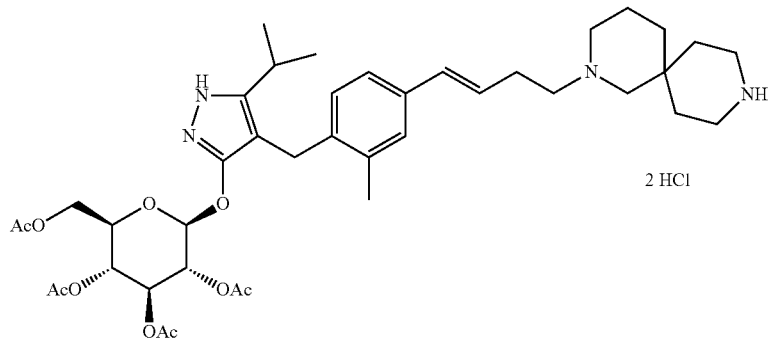
↓ step F
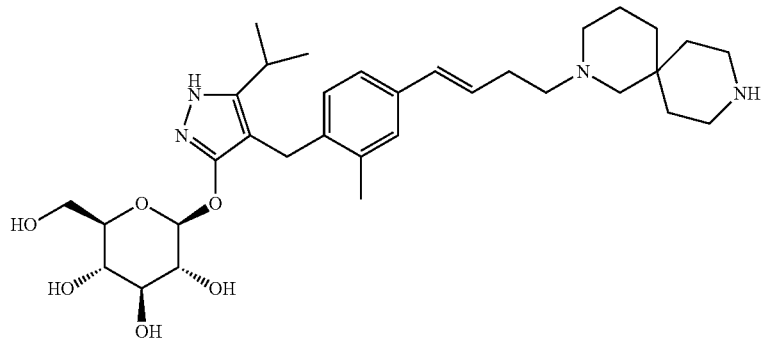

Preparation 9

4-(4-bromo-2-methylbenzyl)-5-(propan-2-yl)-1H-pyrazol-3-yl 2,3,4,6-tetra-O-acetyl-beta-D-glucopyranoside

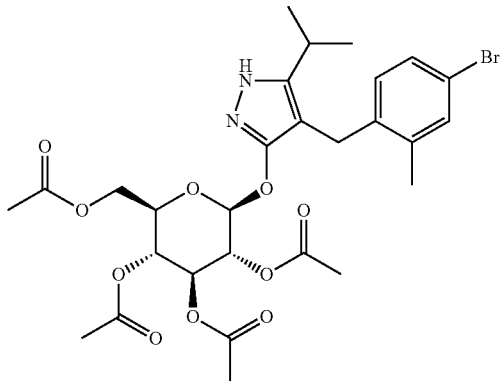 [SMILES: CC(=O)OC[C@H]1O[C@@H](Oc2n[nH]c(C(C)C)c2Cc2ccc(Br)cc2C)[C@H](OC(C)=O)[C@@H](OC(C)=O)[C@@H]1OC(C)=O]

Scheme 2, step A: To a 1 L flask, add 4-[(4-bromo-2-methyl-phenyl)methyl]-5-isopropyl-1H-pyrazol-3-ol (24 g, 77.6 mmol), 2,3,4,6-tetra-O-acetyl-alpha-D-glucopyranosyl bromide (50.4 g, 116 mmol), benzyltributylammonium chloride (5 g, 15.5 mmol), dichloromethane (250 mL), potassium carbonate (32 g, 323 mmol) and water (120 mL). Stir the reaction mixture overnight at room temperature. Extract with dichloromethane (450 mL). Wash extract with water (300 mL) and brine (500 mL). Dry organic phase over sodium sulfate, filter, and concentrate under reduced pressure. Purify the resulting residue by flash chromatography to yield the title compound (36.5 g, 57 mmol). MS (m/z): 638.5 (M+1), 636.5 (M−1).

Alternative Synthesis of 4-(4-bromo-2-methylbenzyl)-5-(propan-2-yl)-1H-pyrazol-3-yl 2,3,4,6-tetra-O-acetyl-beta-D-glucopyranoside Reagents 4-[(4-bromo-2-methyl-phenyl)methyl]-5-isopropyl-1H-pyrazol-3-ol (24.0 g, 77.6 mmol), 2,3,4,6-tetra-O-acetyl-alpha-D-glucopyranosyl bromide (50.4 g, 116 mmol), benzyltributylammonium chloride (4.94 g, 15.52 mmol), potassium carbonate (32.18 g, 232.9 mmol), dichloromethane (250 mL) and water (120 mL) are combined and the mixture is stirred at ambient temperature for 18 hours. The mixture is partitioned between dichloromethane (250 mL) and water (250 mL). The organic phase is washed with brine (250 mL), dried over Na$_2$SO$_4$, filtered, and concentrated under reduced pressure. The resulting residue is purified by flash chromatography (eluting with 10% ethyl acetate in dichloromethane to 70% ethyl acetate in dichloromethane) to give the title compound (36.5 g, 74% yield). MS (m/z): 639/641 (M+1).

Preparation 10

4-{4-[(1E)-4-hydroxybut-1-en-1-yl]-2-methylbenzyl}-5-(propan-2-yl)-1H-pyrazol-3-yl 2,3,4,6-tetra-O-acetyl-beta-D-glucopyranoside

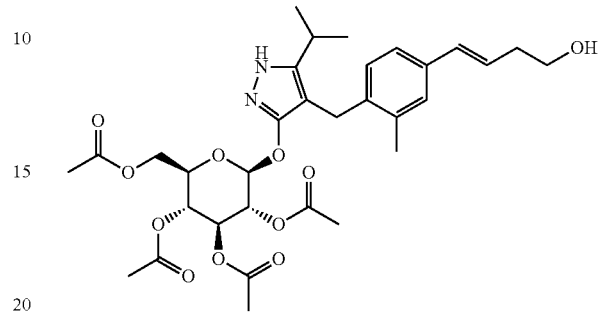

Scheme 2, step B: Add 3-buten-1-ol (6.1 mL, 70 mmol) to a solution of 4-(4-bromo-2-methylbenzyl)-5-(propan-2-yl)-1H-pyrazol-3-yl 2,3,4,6-tetra-O-acetyl-beta-D-glucopyranoside (15 g, 23.5 mmol) in acetonitrile (200 mL) and triethylamine (50 mL). Degas the solution with nitrogen over 10 minutes. Add tri-o-tolylphosphine (1.43 g, 4.7 mmol) and palladium acetate (526 mg, 2.35 mmol). After refluxing at 90° C. for 2 hours, cool, and concentrate to remove the solvent under the reduced pressure. Purify the resulting residue by flash chromatography to yield the title compound (7.5 g, 11.9 mmol). MS (m/z): 631.2 (M+1), 629.2 (M−1).

Preparation 11

4-{4-[(1E)-4-oxybut-1-en-1-yl]-2-methylbenzyl}-5-(propan-2-yl)-1H-pyrazol-3-yl 2,3,4,6-tetra-O-acetyl-beta-D-glucopyranoside

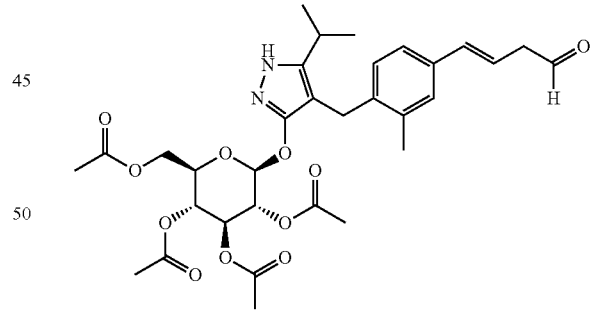

Scheme 2, step C: Add 3,3,3-triacetoxy-3-iodophthalide (2.1 g, 4.76 mmol) to a solution of 4-{4-[(1E)-4-hydroxybut-1-en-1-yl]-2-methylbenzyl}-5-(propan-2-yl)-1H-pyrazol-3-yl 2,3,4,6-tetra-O-acetyl-beta-D-glucopyranoside (1.5 g, 2.38 mmol) and sodium bicarbonate (2 g, 23.8 mmol) in dichloromethane (50 mL) at 0° C. After 15 minutes at room temperature, quench the reaction with saturated aqueous sodium thiosulfate (10 mL). Extract with dichloromethane (30 mL), wash extract with water (30 mL) and brine (40 mL). Dry organic phase over sodium sulfate, filter, and concentrate under reduced pressure. Purify the resulting residue by flash chromatography to yield the title compound (0.95 g, 1.51 mmol). MS (m/z): 628.8 (M+1), 626.8 (M−1).

Preparation 12a tert-butyl 2-{(3E)-4-[3-methyl-4-({5-(propan-2-yl)-3-[(2,3,4,6-tetra-O-acetyl-beta-D-glucopyranosyl)oxy]-1H-pyrazol-4-yl}methyl)phenyl]but-3-en-1-yl}-2,9-diazaspiro[5.5]undecane-9-carboxylate

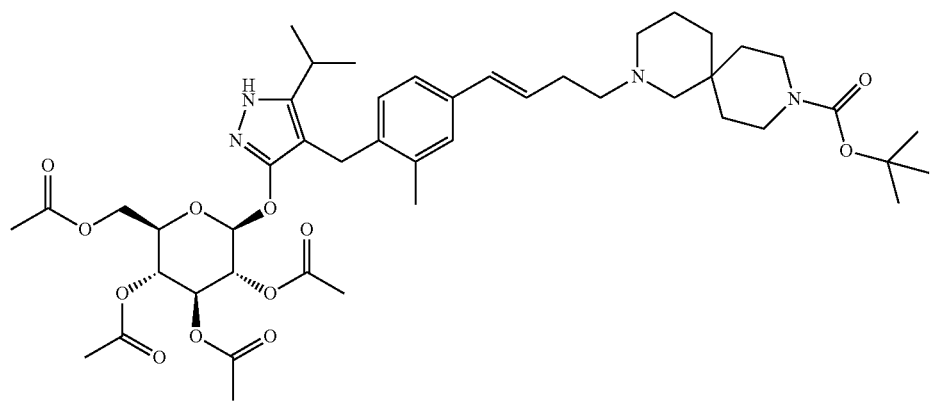 [SMILES: CC(=O)OC[C@H]1O[C@@H](Oc2n[nH]c(C(C)C)c2Cc2ccc(/C=C/CCN3CCCC4(CCN(C(=O)OC(C)(C)C)CC4)C3)cc2C)[C@H](OC(C)=O)[C@@H](OC(C)=O)[C@@H]1OC(C)=O]

Scheme 2, Step D: Add sodium triacetoxyborohydride (303 mg, 1.4 mmol) to a solution of 4-{4-[(1E)-4-oxybut-1-en-1-yl]-2-methylbenzyl}-5-(propan-2-yl)-1H-pyrazol-3-yl 2,3,4,6-tetra-O-acetyl-beta-D-glucopyranoside (600 mg, 0.95 mmol) and tert-butyl 2,9-diazaspiro[5.5]undecane-9-carboxylate hydrochloride (333 mg, 1.2 mmol) in 1,2-dichloroethane (30 mL). After 30 minutes at room temperature, quench the reaction with saturated aqueous sodium bicarbonate (15 mL). Extract with dichloromethane (60 mL). Wash extract with water (30 mL) and brine (60 mL). Dry organic phase over sodium sulfate, filter, and concentrate under reduced pressure. Purify the resulting residue by flash chromatography to yield the title compound (500 mg, 0.58 mmol).

MS (m/z): 866.8, 867.8 (M+1), 864.8, 865.8 (M−1).

Preparation 13

4-{4-[(1E)-4-(2,9-diazaspiro[5.5]undec-2-yl)but-1-en-1-yl]-2-methylbenzyl}-5-(propan-2-yl)-1H-pyrazol-3-yl 2,3,4,6-tetra-O-acetyl-beta-D-glucopyranoside dihydrochloride

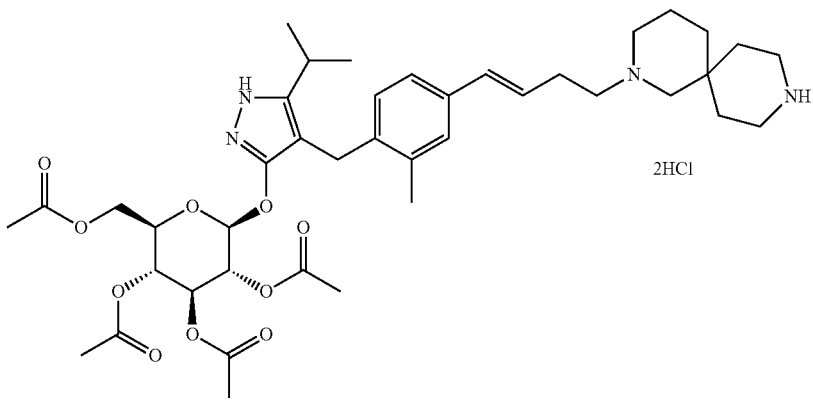 [SMILES: CC(=O)OC[C@H]1O[C@@H](Oc2n[nH]c(C(C)C)c2Cc2ccc(/C=C/CCN3CCCC4(CCNCC4)C3)cc2C)[C@H](OC(C)=O)[C@@H](OC(C)=O)[C@@H]1OC(C)=O]

Scheme 2, step E: Add hydrogen chloride (4.0 M solution in 1,4-dioxane, 1.5 mL, 5.8 mmol) to a solution of tert-butyl 2-{(3E)-4-[3-methyl-4-({5-(propan-2-yl)-3-[(2,3,4,6-tetra-O-acetyl-beta-D-glucopyranosyl)oxy]-1H-pyrazol-4-yl}methyl)phenyl]but-3-en-1-yl}-2,9-diazaspiro[5.5]unde- cane-9-carboxylate (500 mg, 0.58 mmol) in dichloromethane (20 mL). After 2 hours at room temperature, concentrate to remove the solvent under reduced pressure to yield the title compound as a solid (480 mg, 0.57 mmol). MS (m/z): 767.4 (M+1).

Scheme 3

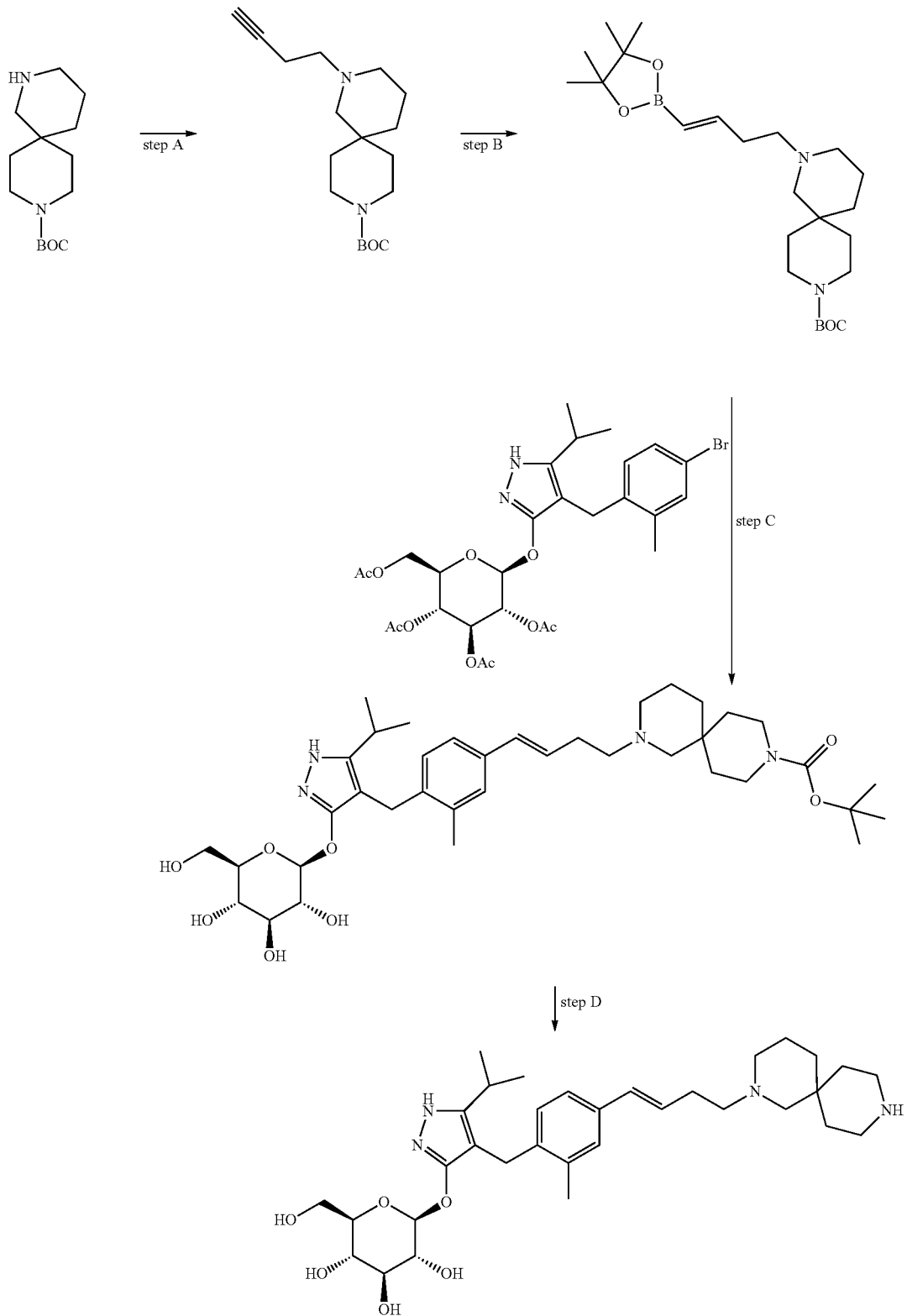

Preparation 14 tert-butyl 4-but-3-ynyl-4,9-diazaspiro[5.5]undecane-9-carboxylate

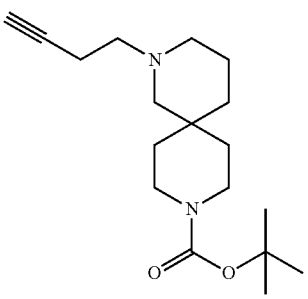 [SMILES: C#CCCN1CCCC2(CCN(C(=O)OC(C)(C)C)CC2)C1]

Scheme 3, step A: Cesium carbonate (46.66 g, 143.21 mmol) is added to a suspension of tert-butyl 4,9-diazaspiro[5.5]undecane-9-carboxylate hydrochloride (16.66 g, 57.28 mmoles) in acetonitrile (167 mL). The mixture is stirred for 10 minutes at ambient temperature then 4-bromobutyne (6.45 mL, 68.74 mmol) is added. The reaction is heated to reflux and stirred for 18 hours. The mixture is cooled and concentrated under reduced pressure. The residue is partitioned between water (200 mL) and ethyl acetate (150 mL). The phases are separated and the aqueous layer is extracted with ethyl acetate (100 mL). The combined organic layers are washed with water (200 mL), then brine (150 mL), dried over MgSO$_4$, filtered, and concentrated under reduced pressure to give the title compound (17.2 g, 98% yield). $^1$H NMR (300.11 MHz, CDCl$_3$): δ 3.43-3.31 (m, 4H), 2.53-2.48 (m, 2H), 2.37-2.29 (m, 4H), 2.20 (s, 2H), 1.94 (t, J=2.6 Hz, 1H), 1.44 (s, 17H).

Preparation 15 tert-butyl 4-[(E)-4-(4,4,5,5-tetramethyl-1,3,2-dioxaborolan-2-yl)but-3-enyl]-4,9-diazaspiro[5.5]undecane-9-carboxylate

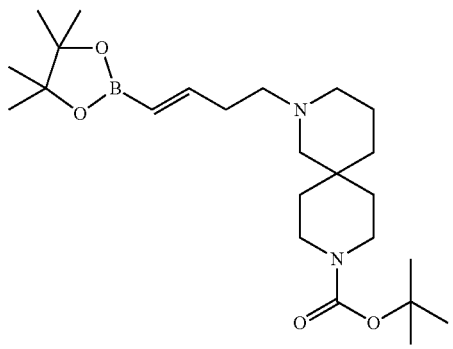 [SMILES: CC(C)(C)OC(=O)N1CCC2(CCCN(CC/C=C/B3OC(C)(C)C(C)(C)O3)C2)CC1]

Scheme 3, step B: Triethylamine (5.62 mmoles; 0.783 mL), 4,4,5,5-tetramethyl-1,3,2-dioxaborolane (8.56 mL, 59.0 mmol) and zirconocene chloride (1.45 g, 5.62 mmoles) are added to tert-butyl 4-but-3-ynyl-4,9-diazaspiro[5.5]undecane-9-carboxylate (17.21 g, 56.16 mmoles). The resulting mixture is heated to 65° C. for 3.5 hours. The mixture is cooled and dissolved in dichloromethane (150 mL). The resulting solution is passed through a ~4 cm thick pad of silica gel, eluting with dichloromethane (2×200 mL). The filtrate is concentrated under reduced pressure to give the title compound (21.2 g, 87% yield). $^1$H NMR (300.11 MHz, CDCl$_3$): δ 6.65-6.55 (m, 1H), 5.49-5.43 (m, 1H), 3.42-3.29 (m, 4H), 2.40-2.27 (m, 6H), 2.25-2.08 (m, 2H), 1.70-1.13 (m, 29H).

Preparation 16 tert-butyl 2-{(3E)-4-[3-methyl-4-({5-(propan-2-yl)-3-beta-D-glucopyranosyl)oxy]-1H-pyrazol-4-yl}methyl)phenyl]but-3-en-1-yl}-2,9-diazaspiro[5.5]undecane-9-carboxylate

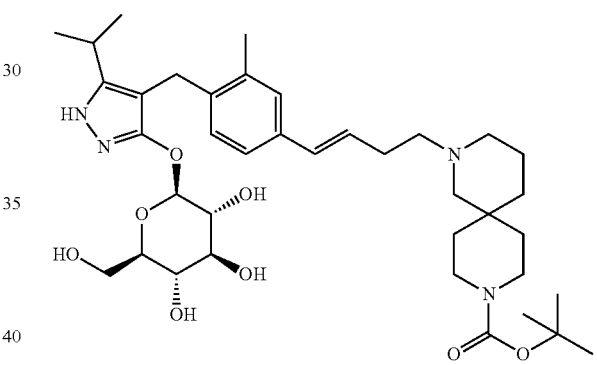

Scheme 3, step C: A solution of 4-(4-bromo-2-methylbenzyl)-5-(propan-2-yl)-1H-pyrazol-3-yl 2,3,4,6-tetra-O-acetyl-beta-D-glucopyranoside (20 g, 31.3 mmol), tert-butyl 4-[(E)-4-(4,4,5,5-tetramethyl-1,3,2-dioxaborolan-2-yl)but-3-enyl]-4,9-diazaspiro[5.5]undecane-9-carboxylate (16.3 g, 37.5 mmol) and potassium carbonate (12.97 g, 93.82 mmol) in tetrahydrofuran (200 mL) and water (40 mL) is degassed for 15 min by bubbling nitrogen gas through it. Pd(OAc)$_2$ (140 mg, 625 μmol) and 2-dicyclohexylphosphino-2',4',6'-tri-i-propyl-1,1'-biphenyl (0.596 g, 1.25 mmol) are added and the reaction is heated to reflux for 16 h. The solution is cooled to ambient temperature and methanol (200 mL) is added. After 30 minutes the solvent is removed under reduced pressure. The mixture is partitioned between ethyl acetate (500 mL) and brine (500 ml) adding aqueous MgSO$_4$ (1M; 500 ml) to aid the phase separation. The layers are separated and the organic layer is dried over MgSO$_4$ and filtered through a 10 cm pad of silica gel, eluting with ethyl acetate (~1.5 L). The filtrate is discarded and the silica pad is flushed with 5% MeOH in THF (2 L). The methanolic filtrate is concentrated under reduced pressure to give the title compound (20.1 g, 92%). MS (m/z): 699 (M+1).

Scheme 4
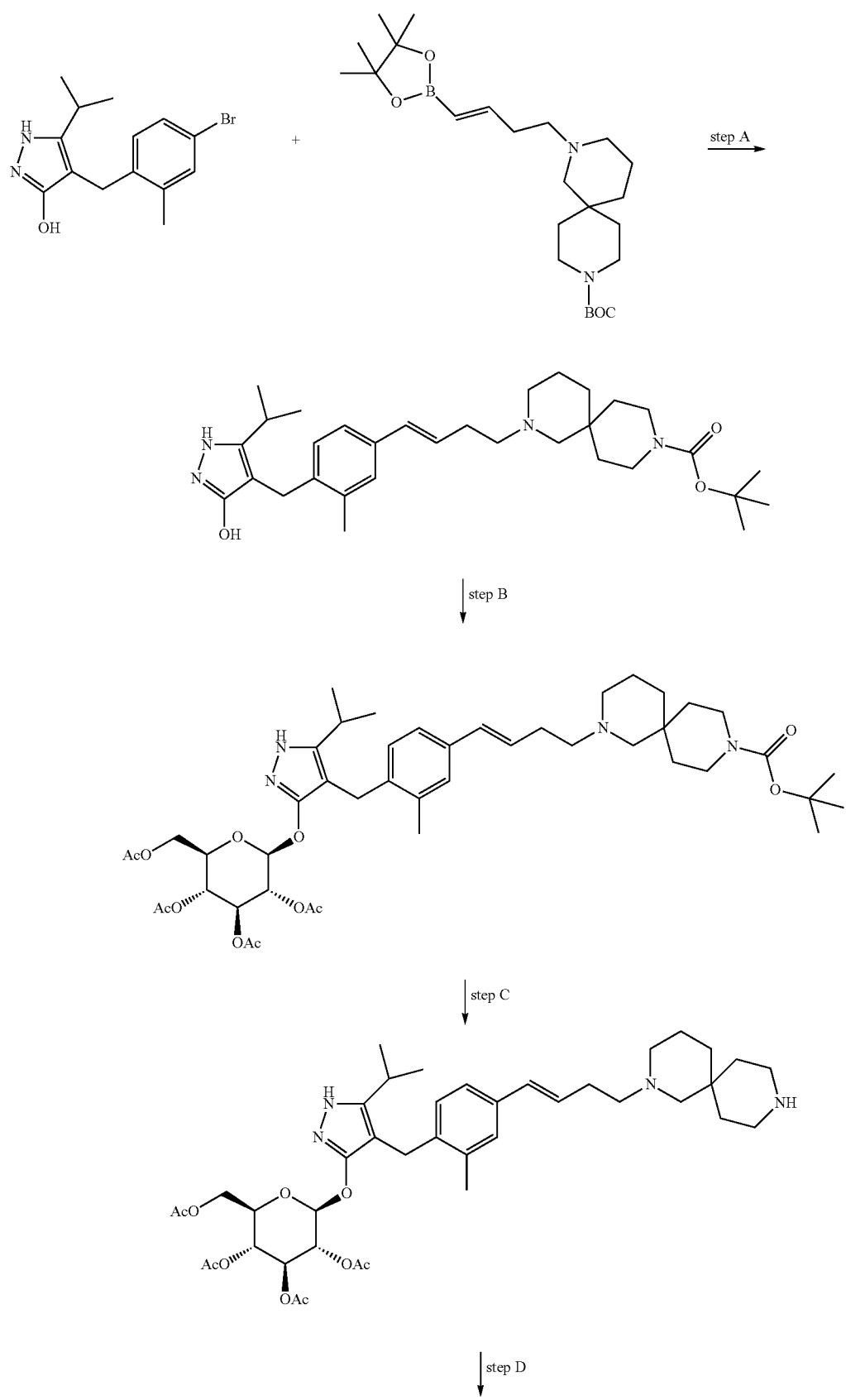

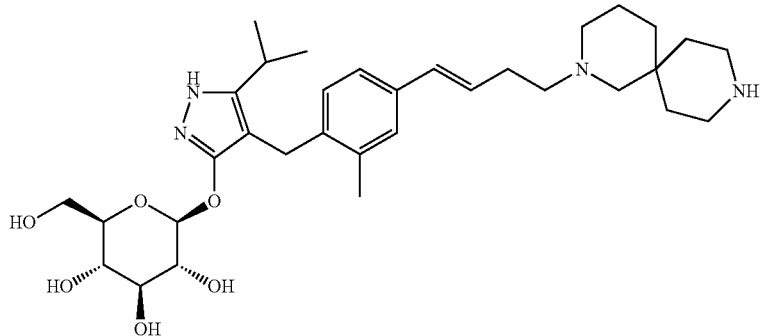 [SMILES: Cc1cc(/C=C/CCN2CCCC3(CCNCC3)C2)ccc1Cc1c(O[C@@H]2O[C@H](CO)[C@@H](O)[C@H](O)[C@H]2O)n[nH]c1C(C)C]

Preparation 17 tert-butyl 4-[(E)-4-[4-[(3-hydroxy-5-isopropyl-1H-pyrazol-4-yl)methyl]-3-methyl-phenyl]but-3-enyl]-4,9-diazaspiro[5.5]undecane-9-carboxylate

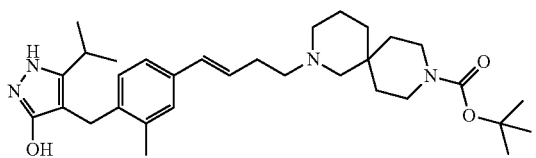 [SMILES: Cc1cc(/C=C/CCN2CCCC3(CCN(C(=O)OC(C)(C)C)CC3)C2)ccc1Cc1c(O)n[nH]c1C(C)C]

Scheme 4, step A: Add tert-butyl 4-[(E)-4-(4,4,5,5-tetramethyl-1,3,2-dioxaborolan-2-yl)but-3-enyl]-4,9-diazaspiro[5.5]undecane-9-carboxylate (35.8 kg, 82.4 mol) in methanol (130 L) to a solution of (4-[(4-bromo-2-methyl-phenyl)methyl]-5-isopropyl-1H-pyrazol-3-ol (23.9 kg, 77.3 mol) in methanol (440 L) at room temperature. Add water (590 L) and tripotassium phosphate (100 kg, 471.7 mol) and place the reaction under nitrogen atmosphere. To the stirring solution, add a suspension of tris(dibenzylideneacetone)dipalladium (1.42 kg, 1.55 mol) and di-tert-butylmethylphosphonium tetrafluoroborate (775 g, 3.12 mol) in methanol (15 L). The resulting mixture is heated at 75° C. for 2 hours. Cool the mixture and filter over diatomaceous earth. Rinse the the filter cake with methanol (60 L), and concentrate the filtrate under reduced pressure. Add ethyl acetate (300 L), separate the layers, and wash the organic layer with 15% brine (3×120 L). Concentrate the organic layer under reduced pressure, add ethyl acetate (300 L), and stir the mixture for 18 to 20 hours. Add heptane (300 L), cool the mixture to 10° C., and stir the mixture for an additional 18 to 20 hours. Collect the resulting solids by filtration, rinse the cake with ethyl acetate/heptane (2:3, 2×90 L), and dry under vacuum at 40° C. to give the title compound (29.3 kg, 70.6% yield) as a white solid. $^1$H NMR (400 MHz, CD$_3$OD): δ 7.14 (s, 1H), 7.07 (d, J=8.0 Hz, 1H), 6.92 (d, J=7.6 Hz, 1H), 6.39 (d, J=16.0 Hz, 1H), 6.25-6.12 (m, 1H), 3.63 (s, 2H), 3.45-3.38 (bs, 3H), 3.34 (s, 3H), 3.33 (s, 3H), 2.85-2.75 (m, 1H), 2.49-2.40 (m, 5H), 2.33 (s, 3H), 1.68-1.62 (m, 2H), 1.60-1.36 (m, 15H), 1.11 (s, 3H), 1.10 (s, 3H).

Preparation 12b

Alternative preparation of tert-butyl 2-{(3E)-4-[3-methyl-4-({5-(propan-2-yl)-3-[(2,3,4,6-tetra-O-acetyl-beta-D-glucopyranosyl)oxy]-1H-pyrazol-4-yl}methyl)phenyl]but-3-en-1-yl}-2,9-diazaspiro[5.5]undecane-9-carboxylate

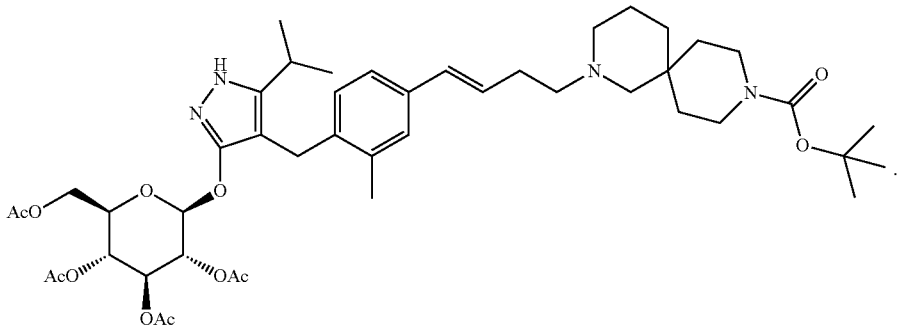 [SMILES: CC(=O)OC[C@H]1O[C@@H](Oc2n[nH]c(C(C)C)c2Cc2ccc(/C=C/CCN3CCCC4(CCN(C(=O)OC(C)(C)C)CC4)C3)cc2C)[C@H](OC(C)=O)[C@@H](OC(C)=O)[C@@H]1OC(C)=O]

Scheme 4, step B: Combine tert-butyl 4-[(E)-4-[4-[(3-hydroxy-5-isopropyl-1H-pyrazol-4-yl)methyl]-3-methyl-phenyl]but-3-enyl]-4,9-diazaspiro[5.5]undecane-9-carboxylate (17.83 kg, 33.2 moles), acetonitrile (180 L), and benzyltributylammonium chloride (1.52 kg, 4.87 moles) at room temperature. Slowly add potassium carbonate (27.6 kg, 199.7 moles) and stir the mixture for 2 hours. Add 2,3,4,6-tetra-O-acetyl-alpha-D-glucopyranosyl bromide (24.9 kg, 60.55 mol), warm the reaction mixture to 30° C. and stir for 18 hours. Concentrate the mixture under reduced pressure and add ethyl acetate (180 L), followed by water (90 L). Separate the layers, wash the organic phase with 15% brine (3×90 L), concentrate the mixture, and purify using column chromatography over silica gel (63 kg, ethyl acetate/heptanes as eluent (1:2→1:0)) to provide the title compound (19.8 kg, 94% purity, 68.8% yield) as a yellow foam. $^1$H NMR (400 MHz, CDCl$_3$): δ 7.13 (s, 1H), 7.03 (d, J=8.0 Hz, 1H), 6.78 (d, J=8.0 Hz, 1H), 6.36 (d, J=16.0, 1H), 6.25-6.13 (m, 1H), 5.64 (d, J=8.0 Hz, 1H), 5.45-5.25 (m, 2H), 5.13-4.95 (m, 2H), 4.84-4.76 (m, 1H), 4.25-4.13 (m, 2H), 4.10-4.00 (m, 2H), 3.90-3.86 (m, 1H), 3.58-3.50 (m, 2H), 3.40-3.22 (m, 4H), 2.89-2.79 (m, 1H), 2.10-1.90 (m, 18H), 1.82 (s, 3H), 1.62-0.82 (m, 22H).

Preparation 18

2-{(3E)-4-[3-methyl-4-({5-(propan-2-yl)-3-[(2,3,4,6-tetra-O-acetyl-beta-D-glucopyranosyl)oxy]-1H-pyrazol-4-yl}methyl)phenyl]but-3-en-1-yl}-2,9-diazaspiro[5.5]undecane

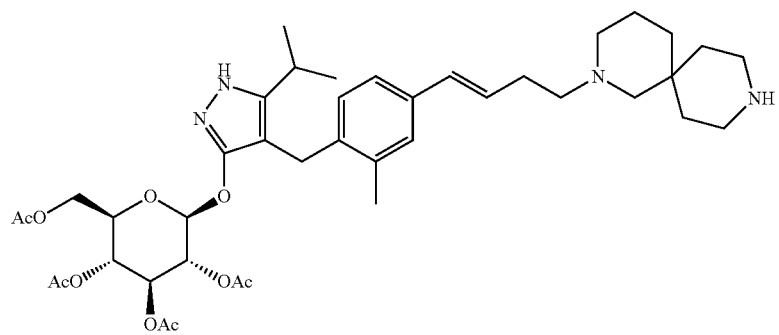 [SMILES: CC(=O)OC[C@H]1O[C@@H](Oc2n[nH]c(C(C)C)c2Cc2ccc(/C=C/CCN3CCCC4(CCNCC4)C3)cc2C)[C@H](OC(C)=O)[C@@H](OC(C)=O)[C@@H]1OC(C)=O]

Scheme 4, step C: Combine tert-butyl 2-{(3E)-4-[3-methyl-4-({5-(propan-2-yl)-3-[(2,3,4,6-tetra-O-acetyl-beta-D-glucopyranosyl)oxy]-1H-pyrazol-4-yl}methyl)phenyl]but-3-en-1-yl}-2,9-diazaspiro[5.5]undecane-9-carboxylate (19.6 kg, 22.6 moles) with dichloromethane (120 L) and cool to 0° C. Slowly add trifluoroacetic acid (34.6 L, 51.6 kg, 452 moles) and stir for 9 hours. Quench the reaction with ice water (80 L), and add ammonium hydroxide (85-90 L) to adjust the reaction mixture to pH (8-9). Add dichloromethane (120 L), warm the reaction mixture to room temperature, and separate the layers. Wash the organic layer with water (75 L), brine, and concentrate under reduced pressure to provide the title compound (16.2 kg, 95.0% purity, 93% yield) as a yellow solid. $^1$H NMR (400 MHz, CDCl$_3$): δ 7.08 (s, 1H), 6.99 (d, J=8.0 Hz, 1H), 6.76 (d, J=7.6 Hz, 1H), 6.38 (d, J=15.6 Hz, 1H), 6.00-5.83 (m, 1H), 5.31 (d, J=7.6 Hz, 1H), 5.25-5.13 (m, 4H), 4.32 (dd, J=12.8, 9.2 Hz, 1H), 4.14 (d, J=11.2 Hz, 1H), 3.90 (d, J=10.0 Hz, 1H), 3.75-3.50 (m, 3H), 3.30-3.00 (m, 5H), 2.85-2.75 (m, 1H), 2.70-2.48 (m, 3H), 2.25 (s, 1H), 2.13-1.63 (m, 19H), 1.32-1.21 (m, 1H), 1.14 (s, 3H), 1.13 (s, 3H), 1.12 (s, 3H), 1.10 (s, 3H).

Example 1

Hydrated crystalline 4-{4-[(1E)-4-(2,9-diazaspiro[5.5]undec-2-yl)but-1-en-1-yl]-2-methylbenzyl}-5-(propan-2-yl)-1H-pyrazol-3-yl beta-D-glucopyranoside acetate First alternative preparation of 4-{4-[(1E)-4-(2,9-diazaspiro[5.5]undec-2-yl)but-1-en-1-yl]-2-methylbenzyl}-5-(propan-2-yl)-1H-pyrazol-3-yl beta-D-glucopyranoside (Free Base)

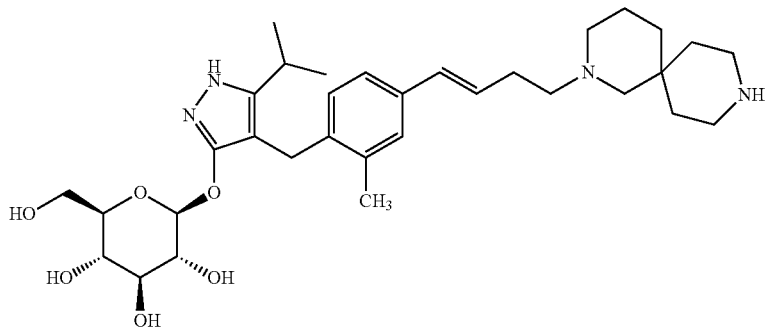 [SMILES: Cc1cc(/C=C/CCN2CCCC3(CCNCC3)C2)ccc1Cc1c(O[C@@H]2O[C@H](CO)[C@@H](O)[C@H](O)[C@H]2O)n[nH]c1C(C)C]

Scheme 1, step I: Add sodium hydroxide (0.5 mL, 0.5 mmol, 1.0 M solution) to a solution of 4-{4-[(1E)-4-(2,9-diazaspiro[5.5]undec-2-yl)but-1-en-1-yl]-2-methylbenzyl}-5-(propan-2-yl)-1H-pyrazol-3-yl 2,3,4,6-tetra-O-benzoyl-beta-D-glucopyranoside dihydrochloride (258 mg, 0.24 mmol) in methanol (2 mL). After 2 hours at 40° C., concentrate to remove the solvent under reduced pressure to give a residue, which is purified by preparative HPLC method: high pH, 25% B for 4 min, 25-40 B % for 4 min @85 mL/min using a 30×75 mm, 5 μm C18XBridge ODB column, solvent A—H$_2$O with NH$_4$HCO$_3$@pH 10, solvent B—MeCN to yield the title compound (free base) as a solid (46 mg, 0.08 mmol). MS (m/z): 598.8 (M+1), 596.8 (M−1).

Second Alternative Preparation of 4-{4-[(1E)-4-(2,9-diazaspiro[5.5]undec-2-yl)but-1-en-1-yl]-2-methylbenzyl}-5-(propan-2-yl)-1H-pyrazol-3-yl beta-D-glucopyranoside (Free Base)

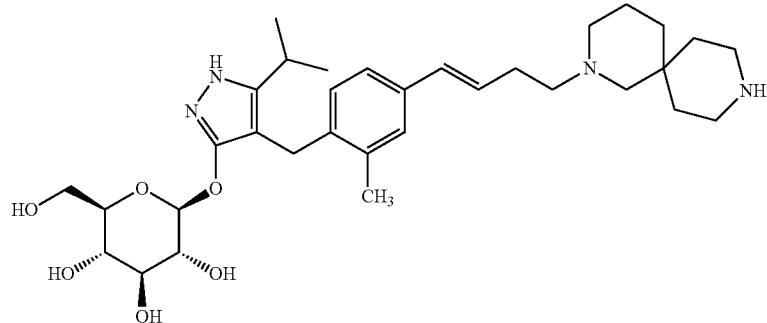 [SMILES: Cc1cc(/C=C/CCN2CCCC3(CCNCC3)C2)ccc1Cc1c(O[C@@H]2O[C@H](CO)[C@@H](O)[C@H](O)[C@H]2O)n[nH]c1C(C)C]

Scheme 2, step F: Add methanol (5 mL), triethylamine (3 mL), and water (3 mL) to 4-{4-[(1E)-4-(2,9-diazaspiro[5.5]undec-2-yl)but-1-en-1-yl]-2-methylbenzyl}-5-(propan-2-yl)-1H-pyrazol-3-yl 2,3,4,6-tetra-O-acetyl-beta-D-glucopyranoside dihydrochloride (480 mg, 0.24 mmol). After 18 hours (overnight) at room temperature, concentrate to dryness under reduced pressure. Purify the resulting residue by preparative HPLC method: high pH, 25% B for 4 min, 25-40 B % for 4 min @85 mL/min using a 30×75 mm, 5 μm C18XBridge ODB column, solvent A—H$_2$O with NH$_4$HCO$_3$@pH 10, solvent B—MeCN to yield the title compound (free base) as a solid (50 mg, 0.08 mmol). MS (m/z): 598.8 (M+1), 596.8 (M−1). $^1$H NMR (400.31 MHz, CD$_3$OD): δ 7.11 (d, J=1.3 Hz, 1H), 7.04 (dd, J=1.3, 8.0 Hz, 1H), 6.87 (d, J=8.0 Hz, 1H), 6.36 (d, J=15.8 Hz, 1H), 6.16 (dt, J=15.8, 6.3 Hz, 1H), 5.02 (m, 1H), 3.81 (d, J=11.7 Hz, 1H), 3.72 (d, J=16.8 Hz, 1H), 3.68 (d, J=16.8 Hz, 1H), 3.64 (m, 1H), 3.37-3.29 (m, 4H), 2.79 (m, 1H), 2.72 (t, J=5.8 Hz, 4H), 2.44-2.33 (m, 6H), 2.30 (s, 3H), 2.26 (broad s, 2H), 1.59 (m, 2H), 1.50 (m, 2H), 1.43 (m, 2H), 1.36 (m, 2H), 1.11 (d, J=7.0 Hz, 3H), 1.10 (d, J=7.0 Hz, 3H).

Third Alternative Preparation of 4-{4-[(1E)-4-(2,9-diazaspiro[5.5]undec-2-yl)but-1-en-1-yl]-2-methylbenzyl}-5-(propan-2-yl)-1H-pyrazol-3-yl beta-D-glucopyranoside Scheme 3, step D: Trifluoroacetic acid (32.2 mL; 0.426 mol) is added to a solution of tert-butyl 2-{(3E)-4-[3-methyl-4-({5-(propan-2-yl)-3-beta-D-glucopyranosyl)oxy]-1H-pyrazol-4-yl}methyl)phenyl]but-3-en-1-yl}-2,9-diazaspiro[5.5]undecane-9-carboxylate (14.87 g; 21.28 mmol) in dichloromethane (149 mL) cooled in iced water. The solution is allowed to warm to room temperature. After 30 minutes, the mixture is slowly added to ammonia in MeOH (2M; 300 mL), applying cooling as necessary to maintain a constant temperature. The solution is stirred at room temperature for 15 min. The mixture is concentrated under reduced pressure and the residue is purified using SCX-2 resin. The basic filtrate is concentrated under reduced pressure and the residue is triturated/sonicated in ethyl acetate, filtered and dried. The resulting solid is dissolved in MeOH (200 mL) and concentrated in vacuo. This is repeated several times to give the title compound (free base) (12.22 g, yield 96%). MS (m/z): 599 (M+1); [α]$_D^{20}$=−12° (C=0.2, MeOH).

Preparation of Final Title Compound, Hydrated Crystalline 4-{4-[(1E)-4-(2,9-diazaspiro[5.5]undec-2-yl)but-1-en-1-yl]-2-methylbenzyl}-5-(propan-2-yl)-1H-pyrazol-3-yl beta-D-glucopyranoside acetate

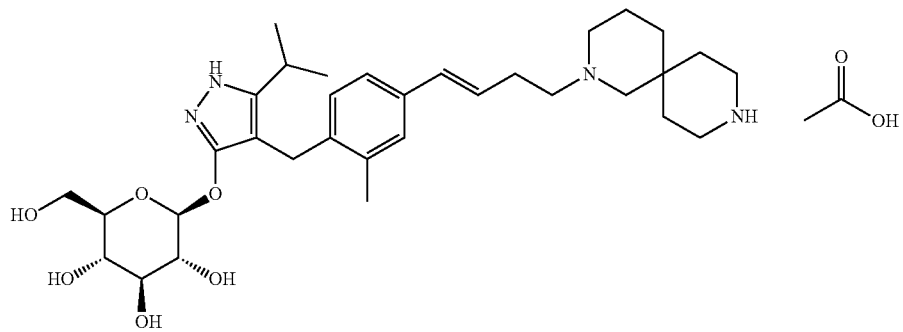

4-{4-[(1E)-4-(2,9-diazaspiro[5.5]undec-2-yl)but-1-en-1-yl]-2-methylbenzyl}-5-(propan-2-yl)-1H-pyrazol-3-yl beta-D-glucopyranoside (902 mg) is placed in a round bottom flask (100 mL) and treated with wet ethyl acetate (18 mL). [Note—wet ethyl acetate is prepared by mixing ethyl acetate (100 mL) and dionized water (100 mL). After mixing, the layers are allowed to separate, and the top wet ethyl acetate layer is removed for use. Acetic acid is a hydrolysis product of ethyl acetate and is present in wet ethyl acetate.] The compound dissolves, although not completely as wet ethyl acetate is added. After several minutes, a white precipitate forms. An additional amount of wet ethyl acetate (2 mL) is added to dissolve remaining compound. The solution is allowed to stir uncovered overnight at room temperature during which time the solvent partially evaporates. The remaining solvent from the product slurry is removed under vacuum, and the resulting solid is dried under a stream of nitrogen to provide the final title compound as a crystalline solid. A small amount of amorphous material is identified in the product by solid-state NMR. This crystalline final title compound may be used as seed crystals to prepare additional crystalline final title compound.

Alternative Preparation of Final Title Compound, Hydrated crystalline 4-{4-[(1E)-4-(2,9-diazaspiro [5.5]undec-2-yl)but-1-en-1-yl]-2-methylbenzyl}-5-(propan-2-yl)-1H-pyrazol-3-yl beta-D-glucopyranoside acetate Under a nitrogen atmosphere combine of 4-{4-[(1E)-4-(2,9-diazaspiro[5.5]undec-2-yl)but-1-en-1-yl]-2-methylbenzyl}-5-(propan-2-yl)-1H-pyrazol-3-yl 2,3,4,6-tetra-O-acetyl-beta-D-glucopyranoside (2.1 kg, 2.74 mol), methanol (4.4 L), tetrahydrofuran (4.2 L), and water (210 mL). Add potassium carbonate (460 g, 3.33 moles) and stir for four to six hours, then filter the reaction mixture to remove the solids. Concentrate the filtrate under reduced pressure, then add ethanol (9.0 L) followed by acetic acid (237 mL, 4.13 mol) and stir at room temperature for one hour. To the stirring solution add wet ethyl acetate (10 L, containing approx. 3 w/w % water) slowly over five hours, followed by water (500 mL). Stir the suspension for twelve hours and add wet ethyl acetate (4.95 L, containing approx. 3 w/w % water) over a period of eight hours. Stir the suspension for twelve hours and add additional wet ethyl acetate (11.5 L, containing approx. 3 w/w % water) slowly over sixteen hours. Stir the suspension for twelve hours, collect the solids by filtration and rinse the solids with wet ethyl acetate (3.3 L, containing approx. 3 w/w % water). Dry in an oven under reduced pressure below 30° C. to give the title compound as an off-white crystalline solid (1.55 kg, 2.35 mol, 96.7% purity, 72.4 w/w % potency, 68.0% yield based on potency). HRMS (m/z): 599.3798 (M+1).

X-Ray Powder Diffraction (XRD)

The XRD patterns of the crystalline solids are obtained on a Bruker D8 Advance X-ray powder diffractometer, equipped with a CuKα source (λ=1.54060 Å) and a Linxeye detector, operating at 40 kV and 40 mA. The sample is scanned between 4 and 40° in 2-theta, with a step size of 0.0084° in 2-theta and a scan rate of 0.5 seconds/step, and with a 0.2 mm divergence slit. The dry powder is packed on a low background silica sample holder and a smooth surface is obtained using a glass slide. The crystal form diffraction patterns are collected at 22° C. and a relative humidity of 42%. It is well known in the crystallography art that, for any given crystal form, the relative intensities of the diffraction peaks may vary due to preferred orientation resulting from certain factors, such as crystal morphology. Where the effects of preferred orientation are present, peak intensities are altered, but the characteristic peak positions of the polymorph are unchanged. See, e.g., The United States Pharmacopeia #23, National Formulary #18, pages 1843-1844, 1995. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of ±0.2 in 2-theta will take into account these potential variations without hindering the unequivocal identification of the indicated crystal form. Confirmation of a crystal form may be made based on any unique combination of distinguishing peaks (in units of ° 2-theta), typically the more prominent peaks. The crystal form diffraction patterns, collected at ambient temperature and relative humidity, are adjusted based on National Bureau of Standards (NBS) 675 standard peaks at 8.853 and 26.774 degrees 2-theta.

A prepared sample of hydrated crystalline 4-{4-[(1E)-4-(2,9-diazaspiro[5.5]undec-2-yl)but-1-en-1-yl]-2-methylbenzyl}-5-(propan-2-yl)-1H-pyrazol-3-yl beta-D-glucopyranoside acetate is characterized by an XRD pattern using CuKα radiation as having diffraction peaks (2-theta values) as described in Table 1 below, and in particular having peaks at 5.2° in combination with one or more of the peaks selected from the group consisting of 7.8°, 8.0°, and 10.7° (±0.2° respectively).

X-Ray Powder Diffraction Peaks of Hydrated Crystalline 4-{4-[(1E)-4-(2,9-diazaspiro[5.5]undec-2-yl) but-1-en-1-yl]-2-methylbenzyl}-5-(propan-2-yl)-1H-pyrazol-3-yl beta-D-glucopyranoside acetate

TABLE 1

| Peak | Angle (°2-Theta) +/− 0.2° | Relative Intensity (% of most intense peak) |
| --- | --- | --- |
| 1 | 5.2 | 100 |
| 2 | 7.8 | 22.6 |
| 3 | 8.0 | 30.4 |
| 4 | 10.1 | 25.6 |
| 5 | 10.5 | 29.8 |
| 6 | 10.7 | 63.8 |
| 7 | 12.0 | 12.8 |
| 8 | 15.0 | 14.3 |
| 9 | 15.8 | 16.7 |
| 10 | 18.6 | 32.4 |
| 11 | 19.8 | 26.5 |
| 12 | 20.9 | 18.2 |

$^{13}$C Solid State NMR ($^{13}$C ssNMR)

$^{13}$C Cross polarization/magic angle spinning NMR (solid-state NMR or ssNMR) spectra were obtained using a Bruker Avance II 400 MHzNMR spectrometer operating at a carbon frequency of 100.622 MHz and proton frequency of 400.131 MHz and equipped with a Bruker 4 mm double resonance probe. TOSS sideband suppression is used along with cross polarization employing SPINAL64 decoupling and a RAMP100 shaped H-nucleus CP pulse. Acquisition parameters are as follows: 90° proton r.f. pulse width of 2.6 μs, contact time was 2.0 ms, pulse repetition time of 3 s, MAS frequency of 10 kHz, spectral width of 30 kHz, acquisition time is 34 ms and the number of scans was 18,661. Chemical shifts are referenced to adamantane (δ=29.5 ppm) in a separate experiment.

Representative $^{13}$C ssNMR resonances for hydrated crystalline 4-{4-[(1E)-4-(2,9-diazaspiro[5.5]undec-2-yl)but-1-en-1-yl]-2-methylbenzyl}-5-(propan-2-yl)-1H-pyrazol-3-yl beta-D-glucopyranoside acetate include: 181.8, 161.2, 160.0, 147.6, 137.4, 135.9, 135.3, 132.6, 131.6, 129.4, 127.3, 126.4, 122.2, 101.9, 99.7, 98.5, 97.9, 78.3, 77.7, 77.2, 76.3, 75.6, 69.1, 68.1, 64.2, 62.6, 60.1, 56.1, 54.2, 41.7, 40.5, 39.1, 34.7, 32.3, 31.5, 31.0, 29.2, 27.8, 26.4, 23.8, 20.8, 19.9, 18.4, and 16.9 ppm (±0.2 ppm respectively).

Sodium-Dependent Glucose Transporter 1 (SGLT1) and SGLT2 Assays

The cDNA encoding human SGLT1 (slc5a1, NM_000343), human SGLT2 (slc5a2, NM_003041) and mouse SGLT1 (slc5a1, NM_019810.4) are purchased from Openbiosystems, Invitrogen and Openbiosystems, respectively. The cDNA is cloned into pcDNA3.1+ for mammalian expression and is stably transfected into Chinese hamster ovary (CHO)-K1 cells using standard mammalian transfection procedures. An SGLT-expressing sub-clone of each over-expressing cell line is selected based on resistance to neomycin (Geneticin, Invitrogen) and activity in the $^{14}$C-α-methyl-D-glucopyranoside ($^{14}$C-AMG) uptake assay (see below). Stable SGLT-expressing cells are maintained using standard cell culture techniques.

The SGLT activity is measured as sodium-dependent $^{14}$C-AMG uptake in the above cell lines described as follows. One hundred µL of culture medium containing 30,000 cells are seeded to each well of a 96-well BioCoat poly-D-lysine plate (Becton Dickson) and cultured at 37° C. overnight. The culture medium is aspirated and cells are washed twice with 200 µL of Reaction Buffer (140 mM NaCl, 2 mM KCl, 1 mM CaCl$_2$, MgCl$_2$, and 14 mM N-2-hydroethylpiperrazine-N'-2-ethanesulfonic acid (Hepes), pH 7.5). The excess buffer is tapped out onto paper towels. Thirty-five µL of Reaction Buffer are added to each well. Five µL of a 10% dimethylsufoxide (DMSO) in Reaction Buffer containing varying concentrations of test compound or no compound as a control, is dispensed into the each well. The reaction is initiated by adding 10 µL of $^{14}$C-AMG in Reaction Buffer to make a final concentration of 4 µM. The plate is incubated at 37° C. for 125 minutes. The reaction is terminated by aspirating off Reaction Buffer and then washed three times with 200 µL of ice cold Reaction Buffer. Manual aspiration is applied to ensure the complete removal of Reaction Buffer. Ten µL of 0.1 N NaOH is added to each well and then 100 µL of Supermix scintillation cocktail (PerkinElmer) is added. After mixing, the scintillation signal in the plate is counted in a MicroBeta (PerkinElmer). A ten-dose response curve is fitted to an empirical four-parameter model using ActivityBase (ID Business Solution) to determine the inhibitor concentration at half-maximal inhibition (IC$_{50}$). The free base of Example 1 is tested essentially as described above.

TABLE 2

In vitro potency of free base of Example 1 against SGLT1 and SGLT2

| Test Compound | Human SGLT1 IC$_{50}$, nM | Human SGLT2 IC$_{50}$, nM | Mouse SGLT1 IC$_{50}$, nM |
|---|---|---|---|
| Example 1 (free base) | 26 ± 20 (n = 10) | 6100 ± 1200 (n = 10) | 10 ± 2 (n = 9) |

More specifically, the data in Table 2 demonstrate that the free base of Example 1 inhibits human and mouse SGLT1 in vitro, and is more potent at human and mouse SGLT1 than at human SGLT2 in vitro.

Glucose Lowering Effects in Oral Glucose Tolerance Test (OGTT)

The test compound is formulated by adding a vehicle of 1% hydroxyethylcellulose, 0.25% Tween® 80 w/antifoam 0.05% to preweighed test compound to make a 1 mg/ml solution. The mixture is probe sonicated for approximately 30 seconds. The resulting solution is used as a stock solution from which the lower concentration dose solutions are prepared by dilution with the vehicle.

Single housed C57B1/6 mice are fasted overnight by removing access to food the late afternoon before test day. The following morning, the mice are weighed and a single fasting blood sample is taken by tail snip to measure glucose by glucometer (Roche AccuChek). Study groups (n=5) are determined based on fasted blood glucose and comprise preferably animals in the range of 80-100 mg/dl glucose.

After grouping, the first mouse is orally gavaged with 10 ml/kg test compound preparation and a timer started. Each subsequent animal is dosed a minute and a half apart. Three hours after the first compound treatment is started, a baseline blood sample is taken for measuring glucose (from the first animal, via tail snip). The animal is then immediately given an oral dose of 50% dextrose (Hospira) at 3 g/kg. Blood samples are taken for glucose, exactly a minute and half apart, by tail vein so that blood is collected in each animal at 20, 40, 60 and 120 minutes after the dextrose dose.

TABLE 3

Glucose lowering effects in OGTT. Oral Glucose Tolerance Test Results Mean ± SE

|  | Vehicle | Example 1 (free base) 0.3 mg/kg | Example 1 (free base) 1 mg/kg | Example 1 (free base) 3 mg/kg | Example 1 (free base) 10 mg/kg |
|---|---|---|---|---|---|
| 2 way ANOVA/Bonferroni's **p < 0.01, ***p < 0.001 compared to vehicle | | | | | |
| Glucose (mg/dl) | | | | | |
| 0 Minute | 84 ± 8.4 | 78 ± 4.2 | 76 ± 3.3 | 72 ± 2.6 | 78 ± 5.4 |
| 20 Minute | 268 ± 49.3 | 185 ± 13.7*** | 147 ± 8.3*** | 133 ± 7.1*** | 124 ± 1.2*** |
| 40 Minute | 192 ± 26.8 | 197 ± 14.7 | 171 ± 11.1 | 150 ± 7.5 | 137 ± 5.4** |
| 60 Minute | 139 ± 6.2 | 164 ± 6.3 | 162 ± 5.8 | 155 ± 7.2 | 138 ± 6.1 |
| 120 Minute | 105 ± 5.1 | 121 ± 11.8 | 109 ± 7.3 | 115 ± 10 | 114 ± 4.3 |
| 1 way ANOVA/Dunnett's *p < 0.05, **p < 0.01, compared to vehicle | | | | | |
| Baseline Adjusted AUC | 6408 ± 1500 | 5400 ± 519 | 4158 ± 374 | 3606 ± 421* | 2693 ± 309** |
| Glucose (mg/dl) | | | | | |
| Glucose Cmax | 268 ± 49.3 | 199 ± 14.1 | 174 ± 9.38** | 161 ± 5.00** | 141 ± 5.67** |
| Time (minutes) | | | | | |
| Glucose Tmax | 20 ± 0 | 32 ± 5 | 48 ± 5 | 64 ± 13** | 44 ± 7 |

As shown above in Table 3, the free base of Example 1 delivers a dose dependent decrease in the glucose excursion following an oral bolus of 50% dextrose (Hospira®) in the normal glycemic C57B1/6 mouse. The free base of Example 1 also demonstrates a dose dependent decrease in baseline adjusted glucose area under the curve (AUC) during an OGTT. In addition, the free base of example 1 dose dependently decreases the average maximum concentration of plasma glucose (Cmax) during the OGTT.

Glucose Values in a Mixed Meal Tolerance Test in Male Rats with Streptozotocin Induced Diabetes Rats which have been administered streptozotocin (STZ) develop diabetes mellitus. Agents which modulate glucose levels in these animals are believed to be useful in the treatment of diabetes in humans.

The test compound is formulated by adding a vehicle of 1% hydroxyethylcellulose (HEC), 0.25% Tween® 80 w/antifoam 0.05% to preweighed test compound to make a 2.5 mg/ml solution. The mixture is probe sonicated for approximately 30 seconds. The resulting solution is used as a stock solution, from which the lower concentration dose solutions are prepared by dilution with the vehicle. STZ, 45 mg/kg, is formulated by dissolving in 0.1M Citrate buffer in 3 ml aliquots and stored in the dark on ice, when not being administered. A high fat content mixed meal (Bio-Serv® Rodent Diet F3282 High Fat) comprising Fat Calories (60%), Carbohydrate Calories (26%) and Protein Calories (15%) is utilized. Single housed Sprague Dawley rats are allowed to acclimate for a period of 3 to 7 days.

In an effort to ensure that the animals have not recently fed, STZ is administered in the afternoon, approximately six hours into the light cycle (lights on 6 am, lights off 6 pm). The animals are anesthetized with isoflurane and STZ is delivered via tail vein injection. Once animals regain consciousness, they are returned to housing and allowed to recover for 7 days.

On the two days immediately prior to the meal tolerance test (MTT) all rats are given a small amount (2-4 g) of the F3282 diet, so they became acclimated to it prior to receiving it during the experiment. On the evening before the experiment, the rats are moved into clean cages and their food is removed. The following morning animals are weighed and a blood sample is taken by tail snip for glucose measurement (Abbott AlphaTRAK™ glucometers: code 29) Animals are grouped n=6 based on fasted body weight and glucose. Thirty minutes after the test compound is orally administered, two glucose measurements are collected. Then a five gram pellet of Bio-Serv® diet 3282 is given. After 20 minutes remaining food is taken away and weighed. Blood samples are taken at 20, 40, 60 and 120 minutes for glucose measurement.

TABLE 4

Glucose values in a mixed MTT in male rats with STZ-induced diabetes.

| Treatment | Dose | 0 min. | 20 min. | 40 min. | 60 min. | 120 min. | Baseline Adjusted AUC |
|---|---|---|---|---|---|---|---|
| Vehicle |  | 113.6 ± 12.6 | 297.2 ± 26.6 | 427.6 ± 41 | 452.2 ± 37.3 | 544.7 ± 50.1 | 36429 ± 3155 |
| Example 1 (free base) | 10 mg/kg | 139 ± 16.1 | 221.2 ± 26.3 | 268.7 ± 29* | 330 ± 36.7 | 490.8 ± 39.2 | 22432 ± 2234* |
| Example 1 (free base) | 30 mg/kg | 137.4 ± 26.9 | 195.4 ± 44.8 | 232 ± 52.2** | 263.9 ± 62.2* | 355.3 ± 73.2* | 14649 ± 3673** |
| Acarbose | 60 mg/kg | 124 ± 16.9 | 181 ± 22.8 | 301.3 ± 51.2 | 371.5 ± 63.9 | 433.7 ± 83 | 23877 ± 4649* |

2 way ANOVA/ Bonferroni's *p < 0.05, **p < 0.01

As shown in Table 4 above, the free base of Example 1 significantly and dose dependently decreases glucose in the MTT compared to the vehicle controls. Acarbose, which is a positive control, did not significantly decrease glucose compared to controls at any time point. Further, there is a dose dependent decrease in glucose baseline adjusted AUCs associated with the free base of Example 1 treatment. Acarbose significantly decreases the glucose AUCs to levels similar to that of Example 1 at 10 mg/kg. Table 4 demonstrates that the free base of Example 1 modulates glucose levels in the male rat.

I claim:
1. A compound of the formula:

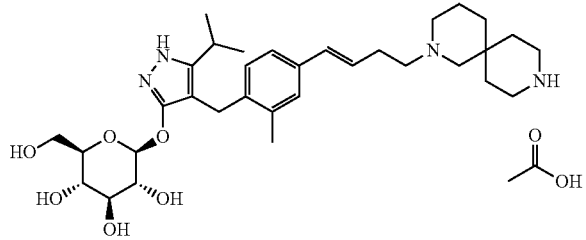

which is a crystalline hydrate.

2. The compound according to claim 1 characterized by at least one of the following:
   a. an X-ray powder diffraction pattern using CuKα radiation having an intense peak at diffraction angle 2-theta of 5.2° in combination with one or more intense peaks selected from the group consisting of 7.8°, 8.0°, and 10.7° (±0.2° respectively); and
   b. a $^{13}$C solid state NMR spectrum which comprises peaks referenced to the highfield resonance of adamantane (δ=29.5 ppm) at: 181.8, 161.2, 160.0, 147.6 and 137.4 ppm (±0.2 ppm respectively).

3. The compound according to claim 1 wherein the water content at ambient temperature is in the range of about 9% to about 12% by weight.

4. A method of treating diabetes in a patient comprising administering to a patient in need of such treatment an effective amount of a compound according to claim 1.

5. A method of treating type 1 diabetes in a patient comprising administering to a patient in need of such treatment an effective amount of a compound according to claim 1.

6. A method of treating type 2 diabetes in a patient comprising administering to a patient in need of such treatment an effective amount of a compound according to claim 1.

7. A pharmaceutical composition comprising a compound according to claim 1 with one or more pharmaceutically acceptable carriers, diluents, or excipients.

* * * * *